(12) United States Patent
Ueno et al.

(10) Patent No.: US 11,780,874 B2
(45) Date of Patent: Oct. 10, 2023

(54) NUCLEOSIDE DERIVATIVE AND USE THEREOF

(71) Applicants: YAMASA CORPORATION, Choshi (JP); National University Corporation Tokai National Higher Education and Research System, Nagoya (JP)

(72) Inventors: Yoshihito Ueno, Gifu (JP); Yusuke Maeda, Gifu (JP); Ryohei Kajino, Gifu (JP)

(73) Assignees: YAMASA CORPORATION, Choshi (JP); NATIONAL UNIVERSITY CORPORATION TOKAI NATIONAL HIGHER EDUCATION AND RESEARCH SYSTEM, Nagoya (JP)

( * ) Notice: Subject to any disclaimer, the term of this patent is extended or adjusted under 35 U.S.C. 154(b) by 519 days.

(21) Appl. No.: 16/760,781

(22) PCT Filed: Oct. 31, 2018

(86) PCT No.: PCT/JP2018/040544
§ 371 (c)(1),
(2) Date: Apr. 30, 2020

(87) PCT Pub. No.: WO2019/088179
PCT Pub. Date: May 9, 2019

(65) Prior Publication Data
US 2020/0385419 A1  Dec. 10, 2020

(30) Foreign Application Priority Data
Oct. 31, 2017  (JP) .................................. 2017-211339

(51) Int. Cl.
C07H 21/02  (2006.01)
C07H 19/10  (2006.01)
C12N 15/113  (2010.01)

(52) U.S. Cl.
CPC ............. *C07H 21/02* (2013.01); *C07H 19/10* (2013.01); *C12N 15/113* (2013.01); *C12N 2310/14* (2013.01)

(58) Field of Classification Search
None
See application file for complete search history.

(56) References Cited

U.S. PATENT DOCUMENTS

| | | |
|---|---|---|
| 5,446,137 A | 8/1995 | Maag et al. |
| 5,681,940 A | 10/1997 | Wang et al. |
| 5,712,378 A | 1/1998 | Wang |
| 6,191,266 B1 | 2/2001 | Wang |
| 6,743,902 B1 | 6/2004 | Wang |
| 2015/0105341 A1 | 4/2015 | Beigelman et al. |
| 2015/0337002 A1 | 11/2015 | Obika et al. |

FOREIGN PATENT DOCUMENTS

| | | | |
|---|---|---|---|
| JP | H05-148293 A | | 6/1993 |
| JP | H10-506915 A | | 7/1998 |
| JP | H10-506915 | * | 9/1998 |
| JP | H11-130793 A | | 5/1999 |
| JP | 2000-512853 A | | 10/2000 |
| JP | 2005-533517 A | | 11/2005 |
| WO | 94/22454 A1 | | 10/1994 |

(Continued)

OTHER PUBLICATIONS

Sep. 9, 2022 Office Action Issued in U.S. Appl. No. 16/470,339.
Dec. 22, 2022 Notice of Allowance issued in U.S. Appl. No. 16/470,339.
Pfundheller et al.; "Oligonucleotides Containing Novel 4'-C- or 3'-C-(Aminoalkyl)-Branched Thymidnes);" Helvetica Chimica Acta; 2000; pp. 128-151; vol. 83.
Gore et al.; "Synthesis, Gene, Silencing, and Molecular Modeling Studies of 4'-C-Aminomethyl-2'-O-methyl Modified Small Interfering RNAs;" The Journal of Organic Chemistry; 2012; pp. 3233-3245; vol. 77.
Pfundheller et al.; "Oligonucleotides Containing 4'-C-Aminomethyl-2'-Modified Thymidines Show Increased Binding Affinity Towards DNA and RNA;" Bioorganic & Medicinal Chemistry Letters; 1999; pp. 2667-2672; vol. 9.

(Continued)

*Primary Examiner* — Traviss C McIntosh, III
(74) *Attorney, Agent, or Firm* — Oliff PLC

(57) ABSTRACT

A nucleoside that is more practical for RNA pharmaceuticals and other applications and use thereof is represented by formula (1) or (2) below, or a salt thereof:

[C1]

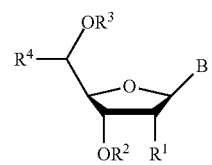

(1)

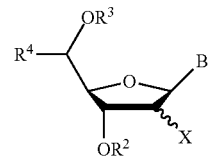

(2)

(In formula (1), $R^1$ represents a hydrogen atom, a hydroxyl group, a hydroxyl group in which a hydrogen atom is substituted by an alkyl group or alkenyl group, or a protected group, and in formula (2), X represents a halogen atom. In formula (1) and formula (2), $R^2$ and $R^3$ may be the same or different, and each represents a hydrogen atom etc., $R^4$ represents $NHR^7$ (in which $R^7$ represents a hydrogen atom etc., and B represent represents any of a purine-9-yl group, 2-oxo-pyrimidin-1-yl group, substituted purine-9-yl group or substituted 2-oxo-pyrimidin-1-yl group).

20 Claims, 3 Drawing Sheets

Specification includes a Sequence Listing.

(56) References Cited

FOREIGN PATENT DOCUMENTS

| WO | 97/048714 A1 | 12/1997 |
|---|---|---|
| WO | 2004/011647 A1 | 2/2004 |
| WO | 2014/112463 A1 | 7/2014 |
| WO | 2015/038596 A1 | 3/2015 |
| WO | 2015/200219 A1 | 12/2015 |
| WO | 2016/106050 A1 | 6/2016 |
| WO | 2017/024310 A1 | 2/2017 |

OTHER PUBLICATIONS

Gore et al.; "Influence of 2'-Fluoro versus 2'-O-Methyl Substituent on the Sugar Puckering of 4'-C-Aminomethyluridine;" The Journal of Organic Chemistry; 2013; pp. 9956-9962; vol. 78.

Prakash et al.; "Identification of metabolically stable 5'-phosphate analogs that support single-stranded siRNA activity;" Nucleic Acids Research; 2015; pp. 2993-3011; vol. 43, No. 6.

Wang et al.; "Biophysical and Biochemical Properties of Oligodeoxy-Nucleotides Containing 4'-C- and 5'-C-Substituted Thymidines;" Bioorganic & Medicinal Chemistry Letters; 1999; pp. 885-890; vol. 9.

Wang et al.; 5'-C-Branched Thymidines: Synthesis, Stereochemistry, and Incorporation Into Oligodeoxynucleotides; Tetrahedron Letters; 1996; pp. 2739-2742; vol. 37, No. 16.

Hampton et al.; "Design of Substrate-Site-Directed Irreversible Inhibitors of Adenosine 5'-Phosphate Aminohydrolase. Effect of Substrate Substituents on Affinity for the Substrate Site;" Journal of Medicinal Chemistry; 1976; pp. 1029-1033; vol. 19, No. 8.

Kajino et al.; "Synthesis and evaluation of siRNA containing aminoalkyl modified nucleosides;" Lecture abstracts of annual conference of Nucleic Acids Therapeutics Society of Japan; 2018; pp. 81; vol. 4.

Kajino et al.; "Synthesis and Properties of siRNA Containing 5'-C-Aminopropyl-2'-O-methyl-nucleosides;" Lecture proceedings of the spring annual conference of the Chemical Society of Japan; 2018; vol. 98.

Kajino et al.; "Synthesis and Property of 5'-C-Aminoalkyl-modified siRNA;" Program & Abstracts, International Symposium on Nucleic Acids Chemistry; 2017; pp. 142-143; vol. 44.

Kajino et al.; "Synthesis and characteristics of saccharide 5'-aminoalkyl-modified siRNA;" Annual Meeting of Union of Chemistry-Related Societies in Chubu Area, Japan; 2017; pp. 81; vol. 48.

Dec. 18, 2018 International Search Report issued in International Patent Application No. PCT/JP2018/040544.

Morita et al.; "Synthesis and Properties of 2'-O,4'-C-Ethylene-Bridged Nucleic Acids (ENA) as Effective Antisense Oligonucleotides"; Bioorganic & Medicinal Chemistry; 2003; pp. 2211-2226; vol. 11.

Jun. 13, 2019 International Preliminary Report on Patentability issued in International Patent Application No. PCT/JP2018/040544.

Pfundheller et al.; "Oligonucleotides Containing Novel 4'-C- or 3'-C-(Aminoalkyl)-Branched Thymidines[1])"; Helvetica Chimica Acta; 2000; pp. 128-151; vol. 83.

Gore et al.; "Synthesis, Gene Silencing, and Molecular Modeling Studies of 4'-C-Aminomethyl-2'-O-methyl Modified Small Interfering RNAs"; The Journal of Organic Chemistry; vol. 77; 2012; pp. 3233-3245.

Ueno, Y. and Matsuda, M.; "Synthesis of Oligonucleotides Modified with Polyamines and Their Properties as Antisense and Antigene Molecules."; Journal of Synthetic Organic Chemistry; vol. 61; 2003; 890-899.

Atsumi et al.; "Nucleosides and Nucleotides. Part 214: Thermal Stability of Triplexes Containing 4'a-C-Aminoalkyl-2'-deoxynucleosides"; Bioorganic & Medicinal Chemistry; vol. 10; 2002; pp. 2933-2939.

Ueno et al.; "Nucleosides and Nucleotides. Part 206: Introduction of Lipophilic Groups into 4'a-C-(2-Aminoethyl) thymidine-Containing Phosphodiester Oligodeoxynucleotides and Thermal Stabilities of the Duplexes"; Tetrahedron; vol. 56; 2000; pp. 7903-7907.

Kanazaki et al.; "Highly Nuclease-Resistant Phosphodiester-Type Oligodeoxynucleotides Containing 4'a-C-Aminoalkylthymidines Form Thermally Stable Duplexes with DNA and RNA. A Candidate for Potent Antisense Molecules"; Journal of the American Chemical Society; vol. 122; 2000; pp. 2422-2432.

Uematsu et al., Synthesis and Properties of 4'-C-Guanidinomethyl-2'-O-methyl Modified RNA; Nucleic Acids Therapeutics Society of Japan; vol. 3; 2017; pp. 88.

Koizumi et al.; "Synthesis and Properties of 4'-C-Aminoalkyl-2'-O-methyl Modified RNA"; Nucleic Acids Therapeutics Society of Japan; vol. 3; 2017; pp. 87.

Maeda et al.; "Synthesis and properties of 4'-C-aminoethyl-2'-F modified nucleic acids"; Nucleic Acids Therapeutics Society of Japan; vol. 3; 2017; pp. 85.

Koizumi et al; "Synthesis and Properties of 4'-C-Aminoalkyl-2'-O-methyl Modified Nucleic Acids"; The Chemical Society of Japan Spring Annual Meeting; vol. 97; Mar. 3, 2017; pp. 85.

Nawale et al.; "Incorporation of 4'-C-aminomethyl-2'-O-methylthymidine into DNA by thermophilic DNA polymerases"; Chemical Communications; vol. 48; 2012; pp. 9619-9621.

Jan. 30, 2018 International Search Report issued in International Patent Application No. PCT/JP2017/044995.

Aug. 15, 2018 International Preliminary Report on Patentability issued in International Patent Application No. PCT/JP2017/044995.

U.S. Appl. No. 16/470,339, filed Jun. 17, 2019 in the name of UENO.

Apr. 20, 2022 Office Action issued in U.S. Appl. No. 16/470,339.

* cited by examiner

NUCLEOSIDE DERIVATIVE AND USE THEREOF

TECHNICAL FIELD

The present Description relates to a nucleoside derivative and a use thereof.

CROSS REFERENCE TO RELATED APPLICATIONS

This application is a related application of Japanese Patent Application No. 2017-211339 which is a Japanese patent application filed on Oct. 31, 2017, and claims priority based on this Japanese application, and all contents described in this Japanese application are incorporated herein by reference.

BACKGROUND ART

Many diseases including cancer are known to be caused by or associated with genetic mutations and abnormal gene expression. RNA drugs such as siRNA that suppress gene expression are useful against such diseases, and are considered to have excellent drug potential.

However, the problem with siRNA and the like is that they have difficulty passing through cell membranes, and are likely to be broken down by nucleases. Consequently, carriers such as LNPs have been used for intracellular delivery of siRNA, and various chemical modifications of nucleosides have also been attempted (Non Patent Literature 1 to 4).

CITATION LIST

Non-Patent Literature 1: HELVATICA CHIMICA ACTA Vol. 83 (2000) 128-151
Non-Patent Literature 2: The Journal of Organic Chemistry 2012, 77, 3233-3245
Non-Patent Literature 3: Bioorganic & Chemistry letters (1999)2667-2672
Non-Patent Literature 4: The Journal of Organic Chemistry 2013, 78, 9956-9962

SUMMARY

Despite such efforts towards cell membrane permeability and nuclease resistance, however, there is still a need for further improvements in the effectiveness of RNA drugs. Even such RNA modifications have not provided satisfactory cell membrane permeability, ribonuclease resistance and gene suppression ability.

It is an object of this Description to provide a nucleoside that is more practical for applications such as RNA pharmaceuticals, along with a use therefor.

Solution to Technical Problem

The inventors focused on chemical modifications to ribose, the sugar part of the ribonucleotide, and also on modifications to the 5' carbon atom, which is a carbon atom of ribose but not a constituent carbon atom of the ribose 5-member ring. We discovered that by introducing a substituent having a base into this 5' carbon atom, it is possible to improve ribonuclease resistance and cell membrane permeability while maintaining gene expression suppression ability. The present Description provides the following means based on these findings.

(1) A nucleoside derivative represented by formula (1) or (2) below, or a salt thereof.

[C1]

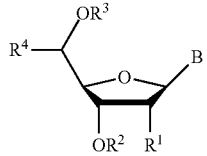

(1)

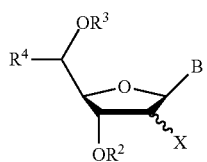

(2)

(In formula (1), $R^1$ represents a hydrogen atom, a hydroxyl group, a hydroxyl group in which a hydrogen atom is substituted by an alkyl group or alkenyl group, or a protected group, and in formula (2), X represents a halogen atom. In formula (1) and formula (2), $R^2$ and $R^3$ may be the same or different, and each represents a hydrogen atom, a hydroxyl protecting group, a phosphate group, a protected phosphate group, or —P(=O)—$R^5R^6$ (in which n is 0 or 1, and $R^5$ and $R^6$ may be the same or different, with each representing a hydrogen atom, hydroxyl group, protected hydroxyl group, mercapto group, protected mercapto group, lower alkoxy group, cyano lower alkoxy group, amino group or substituted amino group, but when n is 1, $R^5$ and $R^6$ are not both hydrogen atoms), $R^4$ represents $NHR^7$ (in which $R^7$ represents a hydrogen atom, an alkyl group, an alkenyl group or a protecting group for an amino group), an azide group, an amidino group or a guanidino group, each having a linking group, and B represents any of a purine-9-yl group, 2-oxo-pyrimidin-1-yl group, substituted purine-9-yl group or substituted 2-oxo-pyrimidin-1-yl group.)

(2) The nucleoside derivative or salt thereof according to (1), wherein in formulae (1) and (2) above, either $R^7$ represents a hydrogen atom or $R^4$ represents the guanidino group having a linking group.

(3) A nucleoside derivative or salt thereof according to (1) or (2), wherein the linking group of $R^4$ in formulae (1) and (2) above is a $C_{1-6}$ alkylene group.

(4) A nucleoside derivative or salt thereof according to any one of (1) to (3), wherein in formulae (1) and (2) above, the linking group of $R^4$ is a $C_{1-6}$ alkylene group, and $R^7$ represents a hydrogen atom.

(5) A cell membrane permeability imparting agent for oligonucleotides, containing a nucleoside derivative according to any one of (1) to (4).

(6) A ribonuclease resistance imparting agent for oligonucleotides, containing a nucleoside derivative according to any one of (1) to (4).

(7) An oligonucleotide derivative or salt thereof, provided with at least one of partial structure selected from the group consisting of formula (3) and formula (4) below.

[C2]

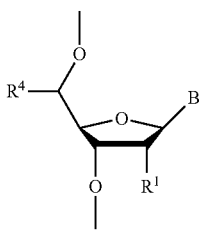

(3)

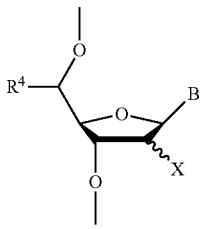

(4)

(In formula (3), $R^1$ represents a hydrogen atom, a halogen atom, a hydroxyl group, a hydroxyl group in which a hydrogen atom is substituted by an alkyl group or alkenyl group, or a protected hydroxyl group, and in formula (4), X represents a halogen atom. In formulae (3) and formula (4), $R^4$ represents $NHR^7$ (in which $R^7$ represents a hydrogen atom, an alkyl group, an alkenyl group or a protecting group for an amino group), an azide group, an amidino group or a guanidino group, each having a linking group, and B represents any of a purine-9-yl group, 2-oxo-pyrimidin-1-yl group, substituted purine-9-yl group or substituted 2-oxo-pyrimidin-1-yl group.)

(8) The oligonucleotide derivative or salt thereof according to (7), provided with at least 2 of the partial structure.

(9) An oligonucleotide derivative or salt thereof according to (7) or (8), provided with a least three of the partial structure.

(10) An oligonucleotide derivative or salt thereof according to any one of (7) to (9), provided with at least 3 and at most 8 of the partial structure.

(11) An oligonucleotide derivative or salt thereof according to any one of (7) to (10), wherein the oligonucleotide is an oligoribonucleotide.

(12) An siRNA agent including an oligonucleotide derivative or salt thereof according to any one of (7) to (11) as an active component.

DESCRIPTION OF EMBODIMENTS

Figure 1:
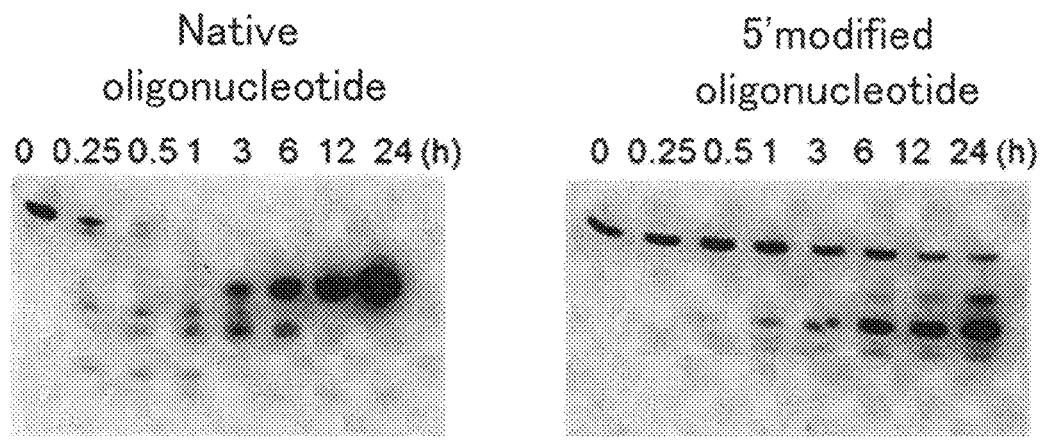
FIG. 1 shows the results of an evaluation of ribonuclease resistance.

The disclosures of this Description relate to a nucleoside derivative or salt thereof that has good utility as an RNA drug such as siRNA, and to a use therefor. With the nucleoside derivative or salt thereof (hereunder sometimes called simply "the nucleoside derivative") disclosed in this Description, adequate gene expression suppression ability is obtained, along with ribonuclease resistance and excellent cell membrane permeability. It is therefore possible to provide an oligonucleotide suitable for administration without using a carrier such as a delivery LNP as in conventional RNA drugs.

The nucleoside derivative is also useful as a reagent such as a detection probe using RNA. That is, an oligonucleotide suited to various RNA reagents can be provided.

The nucleoside derivative disclosed in this Description is based on unexpectedly useful features that were discovered as a result of introducing basic substituents such as aminoalkyl substituents at the 5' position of ribose (which has been difficult to accomplish in the past), and investigating their properties. That is, in the past ribonuclease resistance has commonly been achieved by substitution at the 2' or 3' position of ribose. By contrast, by replacing the hydrogen atom of the 5' carbon atom in the nucleoside derivative disclosed in this Description rather than modifying a carbon atom of the ribose ring, it is possible to maintain the siRNA activity of an oligonucleotide using the nucleoside derivative of the invention while also providing unexpectedly high ribonuclease resistance and cell membrane permeability, which are useful features for an RNA drug or the like.

Typical and non-limiting specific examples of the disclosures of the Description are explained in detail below with reference to the drawings. These detailed explanations are aimed simply at showing preferred examples of the disclosures of the Description in detail so that they can be implemented by a person skilled in the art, and are not intended to limit the scope of the disclosures of the Description. The additional features and disclosures disclosed below may be used separately or together with other features and teachings to provide a further improved nucleoside derivative and use thereof.

The combinations of features and steps disclosed in the detailed explanations below are not essential for implementing the disclosures of the Description in the broadest sense, and are presented only for purposes of explaining typical examples of the disclosures of the Description in particular. Moreover, the various features of the typical examples above and below and the various features described in the independent and dependent claims do not have to be combined in the same way as in the specific examples described here, or in the listed order, when providing addition useful embodiments of the disclosures of the Description.

All features described in the Description and/or Claims are intended as individual and independent disclosures restricting the initial disclosures and the claimed matter specifying the teaching, separately from the constitution of features described in the Examples and/or Claims. Moreover, all descriptions of numerical ranges and groups or sets are intended to include intermediate configurations for purposes of restricting the initial disclosures and the claimed matter specifying the teaching.

(Nucleoside Derivative)

The nucleoside derivative may be a nucleoside derivative represented by formula (1) or formula (2) below, or a salt thereof. This nucleoside derivative may be included in a partial structure of an oligonucleotide by methods well known to those skilled in the art.

[C3]

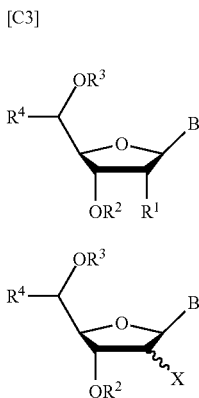

(1)

(2)

Because this nucleoside derivative is provided with a basic substituent at the 5' position of ribose and deoxyribose, it can have charge control properties that allow at least part of the negative charge derived from phosphoric acid groups and the like of the oligonucleotide to be neutralized in an oligonucleotide provided with a partial structure derived from the nucleoside derivative.

The cell membrane permeability of an oligonucleotide provided with such a partial structure can also be improved.

Furthermore, ribonuclease resistance can also be improved in an oligonucleotide provided with a partial structure derived from the nucleoside derivative.

In this Description, "lower" in a substituent of a compound represented by a formula or the like means that the number of carbon atoms constituting the substituent is not more than 10. For example, the number of carbon atoms is normally 1 to 6, or 1 to 5 for example, or 1 to 4, or preferably 1 to 3.

The nucleoside derivative or salt thereof disclosed in this Description is explained below, along with a use therefor.

(Nucleoside Derivative and Salt Thereof)

One embodiment of the nucleoside derivative or salt thereof is a nucleoside derivative or salt thereof represented by formula (1) below.

[C4]

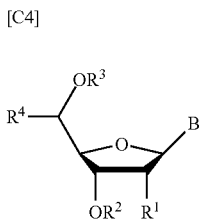

(1)

Another embodiment of the nucleoside derivative or salt thereof is a nucleoside derivative or salt thereof represented by formula (2) below.

[C5]

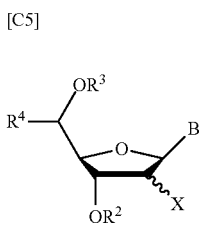

(2)

[$R^1$]

In formula (1), $R^1$ represents a hydrogen atom, a hydroxyl group, a hydroxyl group in which a hydrogen atom is substituted by an alkyl group or alkenyl group, or a protected hydroxyl group. When $R^1$ is a hydrogen atom, the nucleoside derivative is a deoxyribonucleoside derivative. When $R^1$ is a hydroxyl group, a hydroxyl group in which a hydrogen atom is substituted by an alkyl group or alkenyl group, or a protected hydroxyl group, the nucleoside derivative is a ribonucleoside derivative.

[X]

In formula (2), X represents a halogen atom. The halogen atom is not particularly limited, but may be a chlorine atom, iodine atom, fluorine atom, bromine atom or the like. When X is a halogen atom, the nucleoside derivative is a deoxyribonucleoside. As is clear from formula (2), although the bond direction of the halogen atom to the 2' carbon atom of ribose is not particularly limited, the halogen atom is preferably attached so as to correspond to the hydroxyl group of natural ribose.

(Alkyl Group)

In this Description, an alkyl group may be a saturated hydrocarbon group that is linear, branched, cyclic, or a combination of these. Normally a lower alkyl group is preferred, a $C_{1-6}$ lower alkyl group or $C_{1-5}$ lower alkyl groups is more preferred, and a $C_{1-4}$ or $C_{1-3}$ lower alkyl group is especially desirable. Desirable examples of linear $C_{1-4}$ alkyl groups include methyl, ethyl, n-propyl and n-butyl groups and the like, and of these, a methyl, ethyl or n-propyl group is preferred, a methyl or ethyl group is preferred for example, and a methyl group is preferred for example. Desirable examples of branched $C_{1-4}$ alkyl groups include isopropyl, isobutyl, s-butyl and t-butyl groups and the like, and of these, an isopropyl group is especially desirable. Examples of cyclic $C_{1-4}$ alkyl groups include cyclopropyl, cyclobutyl and cyclopropylmethyl groups and the like.

(Alkenyl Group)

In this Description, an alkenyl group may be a saturated hydrocarbon group that is linear, branched, cyclic, or a combination of these. Normally a lower alkenyl group is preferred, and examples of lower alkenyl groups include ethenyl, 1-propenyl, 2-propenyl, 1-methyl-2-propenyl, 1-methyl-1-propenyl, 2-methyl-1-propenyl, 1-butenyl and 2-butenyl groups and the like.

(Hydroxyl Protecting Group or Protected Hydroxyl Group)

In this Description, a hydroxyl protecting groups may be one well known to those skilled in the art, and "Protective Groups in Organic Synthesis" (John Wiley and Sons, 2007) may be consulted for example. Typical examples of hydroxyl protecting groups include aliphatic acyl groups, aromatic acyl groups, lower alkoxymethyl groups, oxycarbonyl groups optionally having suitable substituents, tetrahydropyranyl groups optionally having suitable substituents, tetrathiopyranyl groups optionally having suitable substituents, methyl groups substituted with aryl groups that may be unsubstituted or have 1 to 3 substituents in total (in which a substituent in the substituted aryl group is a lower alkyl, a lower alkoxy, a halogen atom or a cyano group), or silyl groups or the like.

In this Description, an alkoxy group may be a saturated alkyl ether group that is linear, branched, cyclic, or a combination of these. A lower alkoxy group is preferred, and examples of lower alkoxy groups include $C_{1-6}$ lower alkoxy groups or $C_{1-5}$ lower alkoxy groups, of which a $C_{1-4}$ or $C_{1-3}$ alkoxy group is preferred, and a $C_{1-4}$ alkoxy group is especially preferred. Examples of $C_{1-4}$ alkoxy groups include methoxy, ethoxy, n-propoxy and n-butoxy groups and the like. Other preferred examples include isopropoxy, isobutoxy, s-butoxy and t-butoxy groups and the like. Other preferred examples include cyclopropoxy, cyclobutoxy and cyclopropylmethoxy groups and the like.

In this Description, an alkylthio group may be a saturated alkylthio group that is linear, branched, cyclic, or a combination of these. A lower alkylthio group is preferred, a $C_{1-6}$ or $C_{1-5}$ lower alkylthio group is preferred as a lower alkylthio group for example, and a $C_{1-4}$ lower alkylthio group or $C_{1-3}$ alkylthio group is especially preferred. Preferred examples of $C_{1-4}$ saturated alkylthio groups include methylthio, ethylthio, n-propylthio and n-butylthio groups and the like. Other preferred examples include isopropylthio, isobutylthio, s-butylthio and t-butylthio groups and the like. Other preferred examples include cyclopropylthio and cyclobutylthio groups, and a cyclopropylmethylthio group is still more preferred.

Of these, especially preferred examples include aliphatic acyl groups, aromatic acyl groups and silyl groups. A methyl group substituted with an unsubstituted aryl group or an aryl group having 1 to 3 substituents in total (in which the substitutes of the substituted aryl are as described above) is also a preferred example.

Examples of the aliphatic acyl groups include alkylcarbonyl, carboxyalkylcarbonyl, halogeno lower alkyl carbonyl and lower alkoxy lower alkylcarbonyl groups.

The alkyl in the alkylcarbonyl group is as discussed above. That is, examples of alkylcarbonyl groups include formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, eicosanoyl and heneicosyl groups. Of these, an acetyl, propionyl, butyryl, isobutyryl, pentanoyl or pivaloyl group is preferred, and an acetyl group is especially preferred. The alkyl in the carboxylated alkylcarbonyl group is as described above. The substitution position of carboxylation and the like may be selected appropriately. That is, examples of carboxylated alkylcarbonyl groups include succinoyl, glutaroyl and adipoyl groups.

The terms halogen, lower and alkyl in the halogeno lower alkylcarbonyl group are as explained above. The substitution position and the like of the halogen may also be selected appropriately. That is, examples of halogeno lower alkylcarbonyl groups include chloroacetyl, dichloroacetyl, trichloroacetyl and trifluoroacetyl groups.

The terms alkoxy, alkyl and lower in the lower alkoxy lower alkylcarbonyl group are as explained above. The substitution position and the like of the lower alkoxy can also be selected appropriately. That is, the lower alkoxy lower alkylcarbonyl group may be a methoxyacetyl group for example.

Examples of the aromatic acyl groups include arylcarbonyl, halogeno arylcarbonyl, lower alkylated arylcarbonyl, lower alkoxylated arylcarbonyl, carboxylated arylcarbonyl, nitrated arylcarbonyl and arylated arylcarbonyl groups.

Examples of the arylcarbonyl groups include benzoyl, α-naphthoyl and β-naphthoyl groups, and a benzoyl group is especially preferred. Examples of the halogeno arylcarbonyl groups include 2-bromobenzoyl and 4-chlorobenzoyl groups. Examples of the lower alkylated arylcarbonyl groups include 2,4,6-trimethylbenzoyl, 4-toluoyl, 3-toluoyl and 2-toluoyl groups. Examples of the lower alkoxylated arylcarbonyl group include 4-anisoyl, 3-anisoyl and 2-anisoyl groups.

Examples of the carboxylated arylcarbonyl groups include 2-carboxybenzoyl, 3-carboxybenzoyl and 4-carboxybenzoyl groups. Examples of the nitrated arylcarbonyl groups include 4-nitrobenzoyl, 3-nitrobenzoyl and 2-nitrobenzoyl groups. An example of an arylated arylcarbonyl group is 4-phenylbenzoyl.

Examples of the lower alkoxymethyl groups include methoxymethyl, 1,1-dimethyl-1-methoxymethyl, ethoxymethyl, propoxymethyl, isopropoxymethyl, butoxymethyl and t-butoxymethyl groups. A methoxymethyl group is especially preferred.

Examples of the oxycarbonyl groups optionally having suitable substituents include lower alkoxycarbonyl groups, lower alkoxycarbonyl groups substituted with halogens or silyl groups, and alkenyl oxycarbonyl groups.

Examples of the lower alkoxycarbonyl groups include methoxycarbonyl, ethoxycarbonyl and t-butoxycarbonyl isobutoxcarbonyl groups. Examples of the lower alkoxycarbonyl groups substituted with halogens or silyl groups include 2,2-trichloroethoxycarbonyl and 2-(trimethylsilyl)ethoxycarbonyl groups.

Examples of the alkenyl oxycarbonyl groups include vinyloxycarbonyl groups. Desirable example of the tetrahydropyranyl groups optionally having suitable substituents include tetrahydropyran-2-yl or 3-bromotetrahydropyran-2-yl, and tetrahydropyran-2-yl is especially desirable.

Examples of the tetrathiopyranyl groups optionally having suitable substituents include tetrahydrothiopyran-2-yl and 4-methoxytetrahydrothiopyran-4-yl, and tetrahydrothiopyran-2-yl is especially desirable. In a methyl group substituted with an aryl group optionally having 1 to 3 substituents in total, examples of the substituent of the substituted or unsubstituted aryl include lower alkyl and lower alkoxy groups, halogens, and cyano groups.

Examples of methyl groups substituted with aryl groups optionally having 1 to 3 substituents in total include benzyl, α-naphthylmethyl, β-naphthylmethyl, diphenylmethyl, triphenylmethyl and α-naphthyldiphenylmethyl groups, and a benzyl or triphenylmethyl group is preferred. Other examples include 9-anthrylmethyl-4-methylbenzyl, 2,4,6-trimethylbenzyl and 3,4,5-trimethylbenzyl groups, and a 2,4,6-trimethylbenzyl or 3,4,5-trimethylbenzyl group is preferred. Other examples include 4-methoxybenzyl, 4-methoxyphenyldiphenylmethyl and 4,4'-dimethoxytriphenylmethyl groups, and a 4-methoxybenzyl, 4-methoxyphenyldiphenylmethyl group, and 4,4'-dimethoxytriphenylmethyl groups are preferred. Other examples include 4-chlorobenzyl and 4-bromobenzyl groups. Another preferred example is a 4-cyanobenzyl group.

Examples of silyl groups in this Description include trimethylsilyl, triethylsilyl, isopropyldimethylsilyl, t-butyldimethylsilyl, methyldiisopropylsilyl, methyldi-t-butylsilyl, triisopropylsilyl, diphenylmethylsilyl, diphenylbutylsilyl and diphenylisopropylsilyl phenyldiisopropylsilyl groups and the like. Of these, a trimethylsilyl, t-butyldimethylsilyl, triisopropylsilyl or diphenylmethylsilyl group is preferred, and a trimethylsilyl, t-butyldimethylsilyl or diphenylmethylsilyl group is especially preferred.

A hydroxyl protecting group in this Description may mean a substituent that is cleaved and eliminated by either chemical methods (for example, hydrogenolysis, hydrolysis, electrolysis, photolysis, etc.) or biological methods (for example, hydrolysis in the human body, or theoretically induction in microorganisms, etc.). Substituents that are eliminated by hydrogenolysis or hydrolysis are especially desirable as hydroxyl protecting groups. Note that a protected hydroxyl group can be said to be a hydroxyl group in which such a protective group is substituted for a hydrogen atom.

[$R^2$ and $R^3$]

In formula (1) and formula (2), $R^2$ and $R^3$ may be the same or different, and each represents a hydrogen atom, a hydroxyl protecting group, a phosphate group, a protected phosphate group, or —$P(=O)_a(R^5)R^6$. The hydroxyl protecting group was already explained above.

(Protected Phosphate Group)

Protecting groups in protected phosphate groups are well known to those skilled in the art, and the above reference literature and explanations may be consulted.

Examples of protecting groups for phosphate groups include lower alkyl groups, lower alkyl groups substituted with cyano groups, ethyl groups substituted with silyl groups, lower alkyl groups substituted with halogens, lower alkenyl groups, lower alkenyl groups substituted with cyano groups, cycloalkyl groups, lower alkenyl groups substituted with cyano groups, aralkyl groups, aralkyl groups with nitro groups substituted on the aryl ring, aralkyl groups with halogens substituted on the aryl ring, aryl groups substituted with lower alkyl groups, aryl groups substituted with halogens, and aryl groups substituted with nitro groups.

Examples of the lower alkyl groups are as described above. Examples of the lower alkyl groups substituted with cyano groups include 2-cyanoethyl and 2-cyano-1,1-dimethylethyl groups, and a 2-cyanoethyl group is especially preferred. Examples of the ethyl groups substituted with silyl groups include 2-methyldiphenylsilylethyl, 2-trimethylsilylethyl and 2-triphenylsilylethyl groups.

Examples of the lower alkyl groups substituted with halogens include 2,2,2-trichloroethyl, 2,2,2-tribromoethyl, 2,2,2-trifluoroethyl and 2,2,2-trichloroethyl groups, and a 2,2,2-trichloroethyl group is especially preferred. Examples of the lower alkenyl groups include ethenyl, 1-propenyl, 2-propenyl, 1-methyl-2-propenyl, 1-methyl-1-propenyl, 2-methyl-1-propenyl, 1-butenyl and 2-butenyl groups and the like.

Examples of the lower alkenyl groups substituted with cyano groups include 2-cyanoethyl, 2-cyanopropyl and 2-cyanobutenyl groups. Examples of the aralkyl groups include benzyl, α-naphthylmethyl, β-naphthylmethyl, indenylmethyl, phenanthrenylmethyl, anthracenylmethyl, diphenylmethyl, triphenylmethyl, 1-phenethyl, 2-phenethyl, 1-naphthylethyl, 2-naphthylethyl, 1-phenylpropyl, 2-phenylpropyl, 3-phenylpropyl, 1-naphthylpropyl, 2-naphthylpropyl, 3-naphthylpropyl, 1-phenylbutyl, 2-phenylbutyl, 3-phenylbutyl and 4-phenylbutyl groups, of which a benzyl group, diphenylmethyl group, triphenylmethyl group, 1-phenethyl group or 2-phenethyl group is more preferred, and a benzyl group is especially preferred.

Examples of the aralkyl groups with nitro groups substituted on the aryl ring include 2-(4-nitrophenyl) ethyl, 0-nitrobenzyl, 4-nitrobenzyl, 2,4-dinitrobenzyl and 4-chloro-2-nitrobenzyl groups and the like.

A protecting group for phosphoric acid in the present Description may mean a substituent that is cleaved and eliminated by either chemical methods (for example, hydrogenolysis, hydrolysis, electrolysis, photolysis, etc.) or biological methods (for example, hydrolysis in the human body, or theoretically induction in microorganisms, etc.). Substituents that are eliminated by hydrogenolysis or hydrolysis are especially desirable as protecting groups for phosphoric acid.

(—$P(=O)_a(R^5)R^6$)

The $R^2$ and $R^4$ of the nucleoside analog of the present Description may be —$P(=O)_a(R^5)R^6$, in which n is 0 or 1, and $R^5$ and $R^6$ may be the same or different, with each representing a hydrogen atom, hydroxyl group, protected hydroxyl group, mercapto group, protected mercapto group, lower alkoxy group, cyano lower alkoxy group, amino group or substituted amino group. However, when n is 1, $R^5$ and $R^6$ are not both hydrogen atoms. The protected hydroxyl group and lower alkoxy group are as explained above.

(Protected Mercapto Group)

Protected mercapto groups are well known to those skilled in the art. In addition to those given as examples of hydroxyl protecting groups above, examples of protected mercapto groups include alkylthio, arylthio, aliphatic acyl and aromatic acyl groups. An aliphatic acyl or aromatic acyl group is preferred, and an aromatic acyl group is especially preferred. A lower alkylthio group is preferred as an alkylthio group, and desirable examples include methylthio, ethylthio and t-butylthio groups. An example of an arylthio group is a benzylthio group. An example of an aromatic acyl group is a benzoyl group.

Preferred examples of the cyano lower alkoxy group include cyano-group substituted $C_{1-5}$ alkoxy groups (excluding the carbon atoms in the cyano group) that are linear, branched, cyclic, or a combination of these, and specific examples include cyanomethoxy, 2-cyanoethoxy, 3-cyanopropoxy, 4-cyanobutoxy, 3-cyano-2-methylpropoxy and 1-cyanomethyl-1,1-dimethylmethoxy groups and the like, with 2-cyanoethoxy group being especially preferred.

Substituted amino groups may be selected for $R^5$ and $R^6$. The substituent of such an amino group is any of a lower alkoxy group, lower alkylthio group, cyano lower alkoxy group or lower alkyl group. When both $R^5$ and $R^6$ are substituted amino groups, the substituted amino groups may be different from one another. The lower alkoxy, lower alkylthio, cyano lower alkoxy and lower alkyl groups are as explained above.

More specifically, preferred examples of —$P(=O)_a(R^5)R^6$ include phosphoramidite, H-phosphonate and phosphonyl groups, and a phosphoramidite group is especially desirable. —$P(=O)_a(R^5)R^6$ is a phosphoramidite group when n is 0 and at least one of $R^5$ and $R^6$ is a substituted amino group, while the other may be anything. A phosphoramidite group in which one of $R^5$ and $R^6$ is a substituted amino group and the other is a lower alkoxy or cyano lower alkoxy group is especially desirable because it has good reaction efficiency in the condensation reaction. Preferred examples of the substituted amino group include diethylamino, diisopropylamino and dimethylamino groups, and a diisopropylamino group is especially desirable. A preferred example of a lower alkoxy group as the substituent of the other of $R^5$ and $R^6$ is a methoxy group. A preferred example of a cyano lower alkoxy group is a 2-cyanoethyl group. Specific preferred examples of the phosphoramidite include —$P(OC_2H_4CN)(N(CH(CH_3)_2)$ and —$P(OCH_3)(N(CH(CH_3)_2)$.

—$P(=O)_a(R^5)R^6$ is an H-phosphonate group when n is 1 and at least one of $R^5$ and $R^6$ is a hydrogen atom while the other may be anything other than a hydrogen atom. Examples of the substituent other than a hydrogen atom include hydroxy, methyl, methoxy and thiol groups and the like, and a hydroxyl group is especially preferred.

—$P(=O)_a(R^5)R^6$ is a phosphonyl group when n is 1 and $R^5$ and $R^6$ are both lower alkoxy groups. The lower alkoxy groups of $R^5$ and $R^6$ may be the same or different. Preferred examples of these lower alkoxy groups include methoxy and ethoxy groups. A specific example of a phosphonyl group is —P(=O)(OCH$_3$)$_2$.

An especially preferred example of $R^2$ in the nucleoside derivative is —P(=O)$_a$($R^5$)$R^6$. —P(=O)$_a$($R^5$)$R^6$ preferably represents a phosphoramidite group, H-phosphonate group or phosphonyl group. $R^2$ may also preferably be a phosphate group or protected phosphate group. Other preferred examples of $R^2$ include a hydrogen atom and a hydroxyl protecting group.

Other specific examples of $R^2$ include a hydrogen atom, acetyl group, benzoyl group, benzyl group, p-methoxybenzyl group, trimethylsilyl group, tert-butyl diphenylsilyl group, —P(OC$_2$H$_4$CN)(N(CH(CH$_3$)$_2$), —P(OCH$_3$)(N(CH(CH$_3$)$_2$), or a phosphonyl group.

A hydrogen atom or hydroxyl protecting group is preferred as $R^3$ in the nucleoside derivative. A phosphate group, protected phosphate group or —P(=O)$_a$($R^5$)$R^6$ is also desirable for example. As specific examples of $R^3$, a hydrogen atom, acetyl group, benzoyl group, benzyl group, p-methoxybenzyl group, dimethoxytrityl group, monomethoxytrityl group, tert-butyl diphenylsilyl group or trimethylsilyl group is preferred.

[$R^4$]

In formula (1) and formula (2), $R^4$ may represent NHR$^7$, an azide group, an amidino group or a guanidino group, each having a linking group. That is, the NHR$^7$, azide group, amidino group and guanidino group are each linked to the 5' carbon atom via a linking group.

The linking group may represent a divalent hydrocarbon group having 1 or more carbon atoms for example. That is, examples of the divalent hydrocarbon group include $C_{1-8}$ alkylene and $C_{2-8}$ alkenylene groups.

An alkylene group used as a linking group may be linear or branched, but is preferably linear. A lower alkyl group is preferred, such as a $C_{1-6}$ lower alkyl group for example, or preferably a $C_{1-6}$ lower alkyl group, or a $C_{2-4}$ or $C_{2-3}$ lower alkyl group for example. Examples of linear $C_{1-6}$ alkyl groups include methylene, ethylene, propane-1,3-diyl, n-butane-1,1-diyl, n-pentyl-1,5-diyl and n-hexyl-1,6-diyl groups and the like. Other examples include butane-1,2-diyl group and the like. Especially desirable examples include ethylene, propane-1,3-diyl and n-butane-1,1-diyl groups.

An alkenylene group used as a linking group may be linear or branched, but is preferably linear. For example, a lower alkenylene group is preferred, and examples of lower alkenylene groups include ethene-1,2-diyl, propene-1,3-diyl and butene-1,4-diyl groups and the like.

In the nucleoside derivative represented by formula (1), a divalent hydrocarbon group such as an ethylene or other alkylene group with 2 or more carbon atoms is preferred from the standpoint of the nuclease resistance and cell membrane permeability of the oligonucleotide derivative. Moreover, a divalent hydrocarbon group such as an ethylene or other alkylene group with 1 or more carbon atoms is also desirable from the standpoint of nuclease resistance and cell membrane permeability in the nucleoside derivative represented by formula (2).

$R^7$ may be a hydrogen atom, alkyl group, alkenyl group, or amino group protecting group. In addition to the alkyl groups explained above, the alkyl group may preferably be a lower alkyl group. In addition to the alkenyl groups explained above, the alkenyl group may preferably be a lower alkenyl group. If $R^7$ is a hydrogen atom or one of these groups, the linking group is preferably an alkylene group with at least 2, or at least 3, or at least 4 carbon atoms for example, and not more than 6, or not more than 5, or not more than 4 carbon atoms for example.

When $R^7$ is a hydrogen atom, $R^4$ is an NH$_2$ (amino group) having a linking group, which means that when the linking group is an alkylene group or alkenylene group, $R^3$ is an aminoalkyl or aminoalkenyl group. When $R^4$ is an aminoalkyl group or the like in formula (1) and formula (2), the nucleoside derivative and an oligonucleoside derivative provided with monomer units derived from the nucleoside derivative may demonstrate chargeability associated with the property of changing charge depending on the surrounding pH environment. For example, the charge may be cationic under acidic conditions, but the positive charge may be reduced to zero charge in a neutral environment under physiological conditions. That is, due to this charge control ability, the charge of the nucleoside derivative can be made dynamic as necessary or the desired charge can be imparted by changing the pH environment. Consequently, with such a nucleoside derivative of the invention the charge of the oligonucleotide can be controlled in a different way or with a greater degree of freedom than before. For this reason, a nucleoside derivative of the invention in which $R^3$ is such an aminoalkyl group or the like is useful as a charge (positive charge) imparting agent or charge control agent for oligonucleotides and the like.

$R^3$ may be an azide group, an amidino group or in other words CH$_3$(NH)C(NH)— (amidine minus one hydrogen atom from the amino group), or a guanidino group or in other words NH$_2$(NH)C(NH)— (guanidine minus one hydrogen atom from the amino group), each having a linking group. Of these, it may be a guanidino group for example. When $R^3$ has these groups, the linking group may be an alkenylene group or alkylene group having at least 1 or at least 2 carbon atoms for example. When $R^4$ is an amidino group or guanidino group having a linking group, it is always cationic, unlike the case of the aminoalkyl group described above. Such a nucleoside derivative is useful when used in combination with a nucleoside derivative of the invention in which $R^4$ is an aminoalkyl group or the like.

Protecting groups for amino groups are well known to those skilled in the art, and the reference literature described above may be consulted. In addition to those given as examples of hydroxyl protecting groups above, examples include benzyl, methylbenzyl, chlorobenzyl, dichlorobenzyl, fluorobenzyl, trifluoromethylbenzyl, nitrobenzyl, methoxyphenyl, methoxymethyl (MOM), N-methylaminobenzyl, N,N-dimethylaminobenzyl, phenacyl, acetyl, trifluoroacetyl, pivaloyl, benzoyl, phthalimido, allyloxycarbonyl, 2,2,2-trichloroethoxycarbonyl, benzyloxycarbonyl, t-butoxycarbonyl (Boc), 1-methyl-1-(4-biphenyl) ethoxycarbonyl (Bpoc), 9-fluorenylmethoxycarbonyl, benzyloxymethyl (BOM) and 2-(trimethylsilyl) ethoxymethyl (SEM) groups and the like. A benzyl, methoxyphenyl, acetyl, trifluoroacetyl (TFA), pivaloyl, benzoyl, t-butoxycarbonyl (Boc), 1-methyl-1-(4-biphenyl) ethoxycarbonyl (Bpoc), 9-fluorenylmethoxycarbonyl, benzyloxymethyl (BOM) or 2-(trimethylsilyl) ethoxymethyl (SEM) group is preferred, and a benzyl, methoxyphenyl, acetyl, benzoyl or benzyloxymethyl group is especially preferred.

A protecting group of an amino group in the present invention may also mean a substituent that is cleaved and eliminated by either chemical methods (for example, hydrogenolysis, hydrolysis, electrolysis, photolysis, etc.) or biological methods (for example, hydrolysis in the human body, or theoretically induction in microorganisms, etc.). A substituent that is eliminated by hydrogenolysis or hydrolysis is especially desirable as an amino protecting group.

[B: Base]

The B: base in the nucleoside derivative may be a known natural base or an artificial base. For example, B may be selected from a purine-9-yl group, 2-oxo-pyrimidin-1-yl group, substituted purine-9-yl group and substituted 2-oxo-pyrimidin-1-yl group.

That is, examples of B include purine-9-yl and 2-oxo-pyrimidin-1-yl, as well as 2,6-dichloropurin-9-yl and 2-oxo-pyrimidine-1-yl. Other examples include 2-oxo-4-methoxy-pyrimidin-1-yl, 4-(1H-1,2,4-triazol-1-yl)-pyrimidin-1-yl, and 2,6-dimethoxypurin-9-yl.

Other examples include 2-oxo-4-amino-pyrimidin-1-yl in which the amino group is protected, 2-amino-6-bromopurin-9-yl in which the amino group is protected, 2-amino-6-hydroxypurin-9-yl in which the amino group is protected, 2-amino-6-hydroxypurin-9-yl in which the amino group and/or hydroxyl group are protected, 2-amino-6-chloropurin-9-yl in which the amino group is protected, 6-aminopurin-9-yl in which the amino group is protected, and 4-amino-5-methyl-2-oxo-pyrimidin-1-yl in which the amino group is protected. The respective protecting groups of the hydroxyl and amino groups are as explained above.

Other examples include 6-aminopurin-9-yl (adenine), 2-amino-6-hydroxypurin-9-yl (guanidine), 2-oxo-4-amino-pyrimidin-1-yl (cytosine), 2-oxo-4-hydroxypyrimidin-1-yl (uracil) and 2-oxo-4-hydroxy-5-methylpyrimidin-1-yl (thymine).

Still other examples include 4-amino-5-methyl-2-oxo-pyrimidin-1-yl (methylcytosine), 2,6-diaminopurin-9-yl, 6-amino-2-fluoropurin-9-yl, 6-mercaptopyurin-9-yl, 4-amino-2-oxo-5-chloro-pyrimidin-1-yl, and 2-oxo-4-mercapto-pyrimidin-1-yl.

Yet other examples include 6-amino-2-methoxypurin-9-yl, 6-amino-2-chloropurin-9-yl, 2-amino-6-chloropurin-9-yl, and 2-amino-6-bromopurin-9-yl.

The respective substituents in the substituted purine-9-yl group or substituted 2-oxo-pyrimidin-1-yl group may be any of a hydroxyl group, a protected hydroxyl group, a lower alkoxy group, a mercapto group, a protected mercapto group, a lower alkylthio group, an amino group, a protected amino group, an amino group substituted with a lower alkyl group, a lower alkyl group, a lower alkoxymethyl group, a halogen atom, or a combination of these. These substituents have already been explained above.

Substituted purine-9-yl or substituted 2-oxo-pyrimidin-1-yl in which the substituents are those explained above is preferred as B in the nucleoside derivative, but it is also desirable to add a triazole group or lower alkoxymethyl group.

Desirable examples of substituted purine-9-yl include 6-aminopurin-9-yl, 2,6-diaminopurin-9-yl, 2-amino-6-chloropurin-9-yl, 2-amino-6-bromopurin-9-yl, 2-amino-6-hydroxypurin-9-yl, 6-amino-2-methoxypurin-9-yl, 6-amino-2-chloropurin-9-yl, 6-amino-2-fluoropurin-9-yl, 2,6-dimethoxypurin-9-yl, 2,6-dichloropurin-9-yl and 6-mercaptopurin-9-yl. If the substituent contains an amino group or hydroxyl group, desirable examples include substituents in which these amino groups and/or hydroxyl groups are protected.

Examples of substituted 2-oxo-pyrimidin-1-yl include 2-oxo-4-amino-pyrimidin-1-yl, 1H-(1,2,4-triazol-1-yl)-pyrimidin-1-yl, 4-1H-1,4-amino-2-oxo-5-chloro-pyrimidin-1-yl, 2-oxo-4-methoxy-pyrimidin-1-yl, 2-oxo-4-mercapto-pyrimidin-1-yl, 2-oxo-4-hydroxy-pyrimidin-1-yl, 2-oxo-4-hydroxy-5-methylpyrimidin-1-yl, 4-amino-5-methyl-2-oxo-pyrimidin-1-yl and the like. Other desirable examples include 2-oxo-4-methoxy-pyrimidin-1-yl and 4-(1H-1,2,4-triazol-1-yl)-pyrimidin-1-yl.

Of these B bases, desirable examples include substituents in which the amino group or hydroxyl group has been protected if there is an amino group or hydroxyl group in the substituent.

The nucleoside derivative may also be a salt. The form of the salt is not particularly limited, but common examples include acid-addition salts, and the salt may also take the form of an intermolecular counter-ion. Depending on the types of substituents, it may also take the form of a base-addition salt. The salt is preferably a pharmacologically acceptable salt. Types of acids and bases used to form pharmacologically acceptable salts are well known to those skilled in the art, and reference may be made to those described in J. Pharm. Sci., 1-19 (1977) and the like. Examples of acid-addition salts include mineral acid salts and organic acid salts. When one or more substituents contain acidic parts, a base-addition salt may be preferred.

Examples of mineral acid salts include hydrochloride salts, hydrobromide salts, hydroiodide salts, nitrate salts, sulfate salts, hydrogen sulfate salts, phosphate salts, hydrogen phosphate salts and the like. Normally, a hydrochloride salt or phosphate salt is preferred. Examples of organic acid salts include acetate salts, trifluoroacetate salts, gluconate salts, lactate salts, salicylate salts, citrate salts, tartrate salts, ascorbate salts, succinate salts, maleate salts, fumarate salts, formate salts, benzoate salts, methansulfonate salts, ethanesulfonate salts, p-toluenesulfonate salts and the like. Normally, an acetate salt or the like is preferred. Examples of base-addition salts include alkali metal salts, alkali earth metal salts, organic amine salts, and amino acid addition salts.

Examples of the alkali metal salts include sodium salts, potassium salts and the like. Examples of the alkali earth metal salts include magnesium salts, calcium salts and the like. Examples of the organic amine salts include triethylamine salts, pyridine salts, procaine salts, picoline slats, dicyclohexylamine salts, diethanolamine salts, triethanolamine salts, tris(hydroxymethyl) aminomethane salts and the like. Examples of amino acid addition salts include arginine salts, lysine salts, ornithine salts, serine salts, glycine salts, aspartate salts, glutamate salts and the like.

The nucleoside derivative or salt thereof may be in the form of a hydrate or solvate, and these substances are also within the scope of the disclosures of this Description. The nucleoside derivative or salt thereof can be easily manufactured by a person skilled in the art by well-known methods, or following the synthesis examples below.

The nucleoside derivative can improve the nuclease resistance of a single- or double-stranded oligonucleotide when introduced as at least part of an oligonucleotide, and can also improve cell membrane permeability with respect to mammalian cells and the like. That is, the nucleoside derivative is itself useful as a nuclease resistance improving agent and/or cell membrane permeability imparting agent. The nucleoside derivative may also be provided with a basic substituent at the 4' position. It can thus function as a positive charge imparting agent or charge control agent by regulating the negative charge derived from phosphate groups in the oligonucleotide and the like.

(Oligonucleotide Derivative and Salt Thereof)

The oligonucleotide derivative disclosed in this Description (hereunder sometimes called "the oligonucleotide derivative") may contain at least 1 partial structure represented by formula (3) or (4). The partial structures represented by formula (3) and formula (4) can be obtained based on the nucleoside derivatives represented by formulae (1) and (2), respectively, or their salts.

[C6]

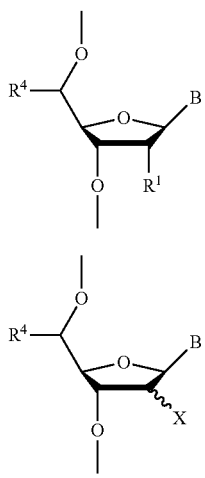

(3)

(4)

R¹, X, R⁴ and B in the partial structures represented by formula (3) and formula (4) are defined as in formula (1) and formula (2).

2 or more of the partial structures represented by formula (3) and formula (4) may also be contained in the oligonucleotide derivative. In this case, these partial structure may be the same or different. Moreover, the total of the partial structures contained in the oligonucleotide derivative may consist only of partial structures represented by formula (3), or only of partial structures represented by formula (4). They may also comprise 1 or 2 or more partial structures represented by formula (3) and 1 or 2 or more partial structures represented by formula (4).

In terms of the arrangement of the partial structures represented by formulae (3) and (4), they may be disposed adjacent to one another or apart from one another. For example, the oligonucleotide derivative of the invention may have at least three of this partial structure. In this case, the partial structures may be provided roughly equally at the 5' end, the center and the 3' end of the oligonucleotide derivative, although this is not necessarily the case. For the partial structure to be provided equally at these positions on the oligonucleotide derivative does not necessarily mean that the same numbers of the partial structure are provided at each position, and it is sufficient that at least one partial structure be provided at each position. For example, if about 1 to 3 of the partial structure are provided at each position, they are considered to be provided equally. When the oligonucleotide derivative is intended as siRNA for example, the chain length thereof is generally 18-mer to 25-mer, or typically 21-mer to 23-mer. The oligonucleotide derivative may be provided with at least 4, or for example 5, or for example 6 of the partial structure. The oligonucleotide derivative may also be provided with not more than 8 for example, or not more than 7 for example, or not more than 6 for example of the partial structure, although this is not a particular limitation.

Since the sugar chain part of the partial structure represented by formula (3) derives from ribose or deoxyribose, the oligonucleotide derivative may be either an oligoribo- nucleotide or an oligodeoxyribonucleotide. This oligonucleotide derivative may also be a chimera comprising both ribonucleotides and deoxyribonucleotides.

The oligonucleotide derivative is itself single-stranded, but it can also assume a hybrid form or in other words a double-stranded form with oligoribonucleotides, oligodeoxyribonucleotides and oligodeoxyribo/ribonucleotides (chimera strands).

The oligonucleotide derivative may also be provided with other partial structures corresponding to natural nucleotides, known nucleoside derivatives and/or known nucleotide derivatives and the like as partial structures other than those represented by formula (3) and formula (4). The partial structures stipulated in this Description and other partial structures may be linked together by phosphate diester linkage, phosphate monoester linkage or thiophosphate ester linkage or the like.

In terms of the number of units of the partial structures and other nucleoside derivatives, the oligonucleotide derivative of the invention may have at least 2 such units, or preferably at least 8, or especially at least 15 such units. There is no particular maximum, but the number of units may be not more than 100, or not more than 80, or not more than 60, or not more than 50, or not more than 40, or not more than 30, or not more than 20 for example.

The oligonucleotide derivative may have one or more asymmetric centers in the partial structures represented by formula (3) and formula (4) as well as in other partial structures, and similarly when stereoisomers exist, the scope of the invention encompasses any mixtures of stereoisomers or racemic mixtures. Tautomers may also be present.

The oligonucleotide derivative may also be a salt. The form of the salt is not particularly limited, and desirable examples include pharmacologically acceptable salts.

Embodiments of the salt of the nucleoside derivative of the invention described above may be applied to the salt. The oligonucleotide derivative or salt thereof may be in the form of a hydrate or solvate, and these are included within the scope of the invention.

(Manufacturing Nucleoside Derivative and Oligonucleotide Derivative)

The nucleoside derivative and oligonucleotide derivative of the invention can be easily synthesized by a person skilled in the art based on the specific synthesis examples below and on known synthesis technology for nucleosides and oligonucleotides as of the date of the application.

The nucleoside derivative and oligonucleotide derivative of the invention can be manufactured by the following methods for example, but the methods for manufacturing the nucleoside analog and oligonucleotide analog of the invention are not limited to the following methods.

The reaction times in the respective reactions are not particularly limited, and because the progress of the reaction can be easily tracked by the analysis methods described below, the reaction may be terminated at the point at which the yield of the target product the greatest.

Moreover, the respective reactions may also be performed in an inactive gas atmosphere such as a nitrogen flow or argon flow as necessary. When protection with a protecting group or subsequent deprotection is necessary in the respective reactions, these reactions may be accomplished appropriately by the methods described below.

In this Description, Bn represents a benzyl group, Ac an acetyl group, Bz a benzoyl group, PMB a p-methoxybenzyl group, Tr a triphenylmethyl group, TBAF a tetrabutyl ammonium fluoride, TEMPO a 2,2,6,6-tetramethylpiperidine 1-oxyl, DDQ a 2,3-dichloro-5,6-dicyano-p-benzoquinone, PPH₃ a triphenylphosphine, BCl₃ a boron trichloride, THA a trifluoroacetyl group, TsO a tosyloxy group, MMTr a 4-methoxytriphenylmethyl group, DMTr a 4,4'-dimethoxytriphenylmethyl group, TMS a trimethylsilyl group, TBDMS a tert-butyl dimethylsilyl group, TBDPS a tert-butyl diphenylsilyl group, MOM a methoxymethyl group, BOM a benzyloxymethyl group, and SEM a 2-(trimethylsilyl) ethoxymethyl group.

For example, one example of the nucleoside derivative can be synthesized according to the following synthesis scheme. This scheme is an example of a scheme for synthesizing a thymine ribonucleoside derivative using glucose as a starting material, and then synthesizing a phosphoramidite agent for synthesizing the oligonucleotide derivative.

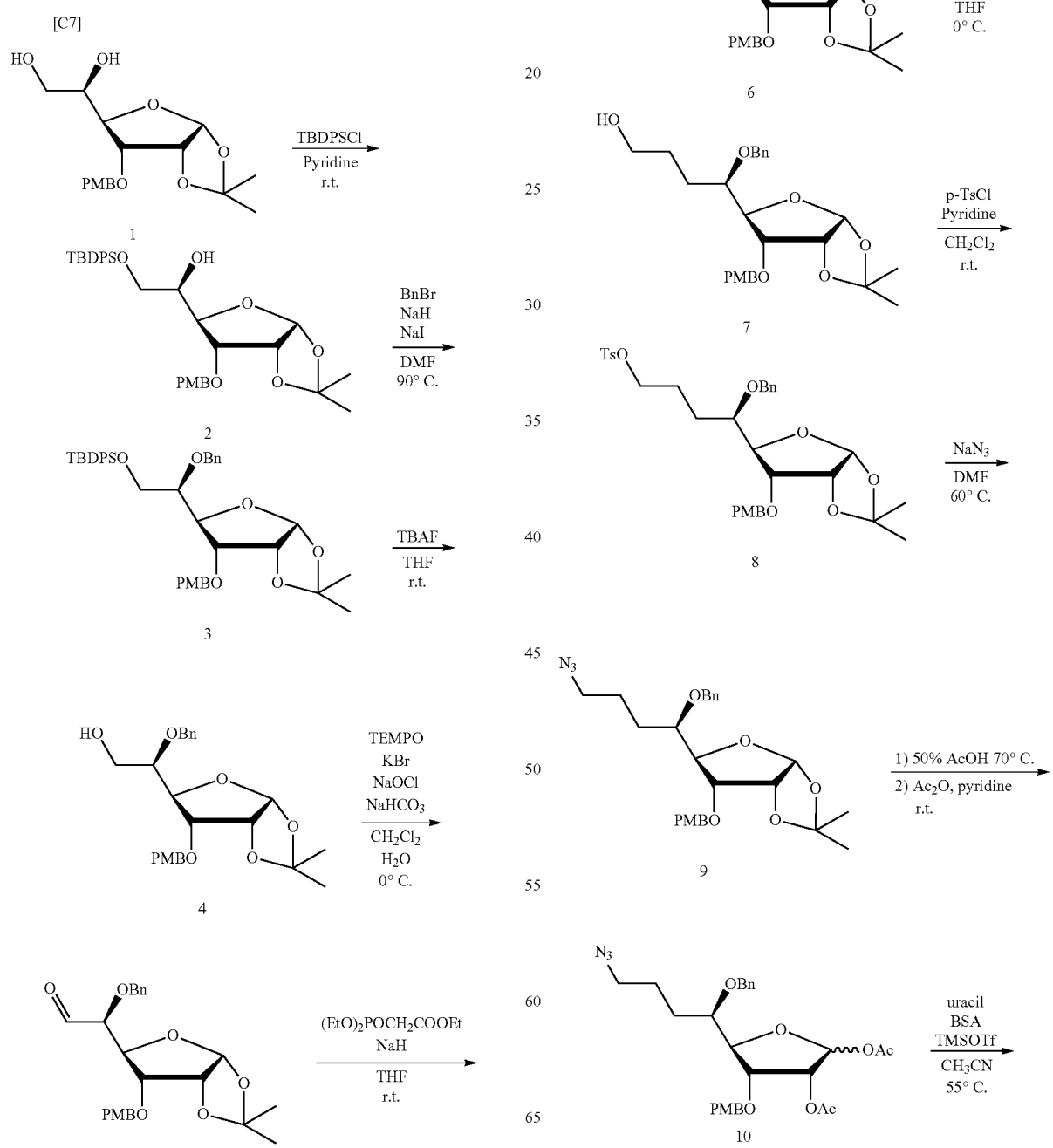

19
-continued

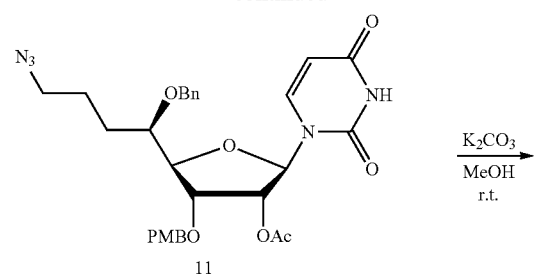
11

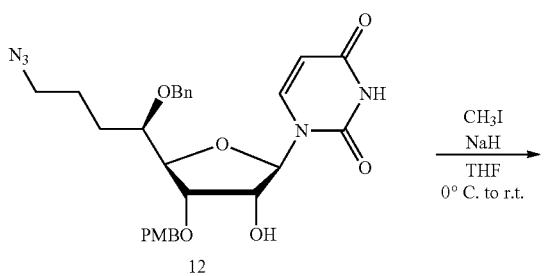
12

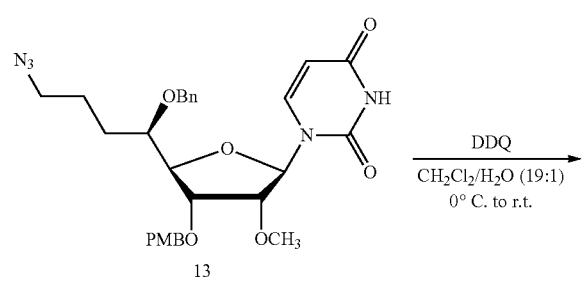
13

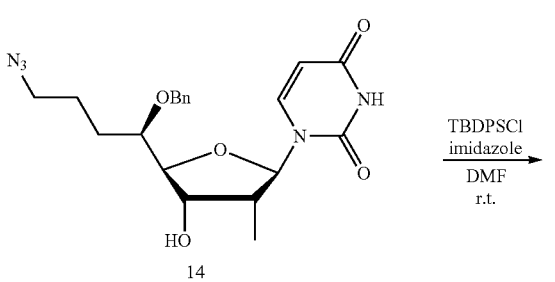
14

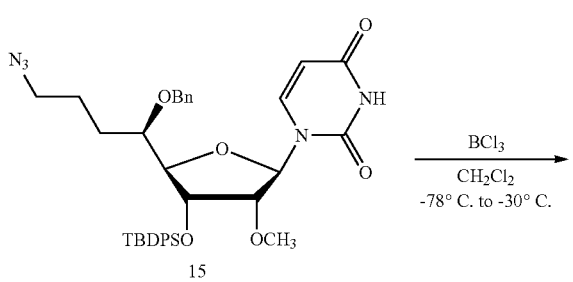
15

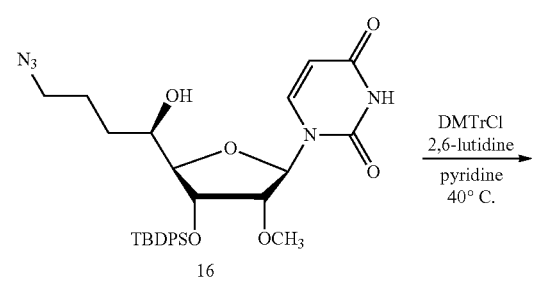
16

20
-continued

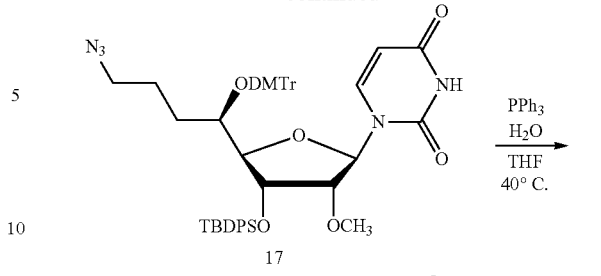
17

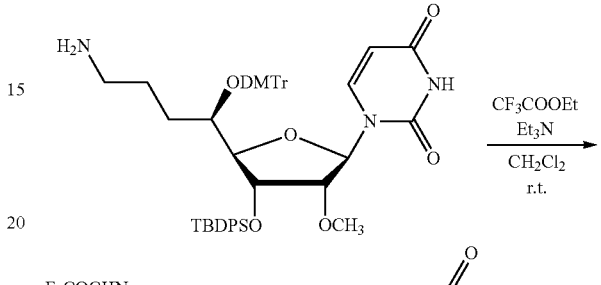

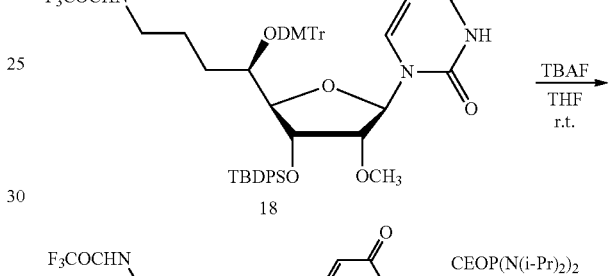
18

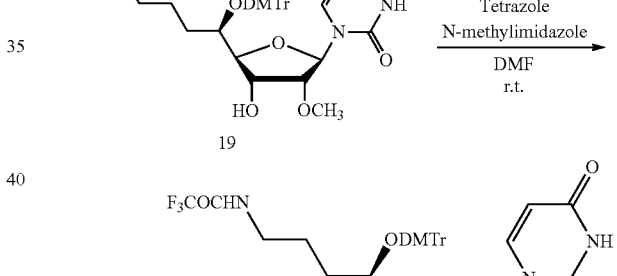
19

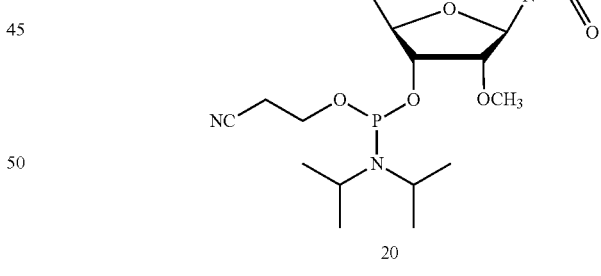
20

The compound 1 was obtained by ordinary methods from glucose. The compounds 3 to 20 can be obtained from the compound 1 based on the descriptions of Bioorganic & Medical Chemistry 11 (2003), 211-2226, Bioorganic & Chemistry Letters (1999), 2667-2672, The Journal of Organic Chemistry 2013, 78, 9956-9962, HELVATICA CHIMICA ACTA Vol. 83 (2000), 128-151 and the like, as well as Bioorganic & Medical Chemistry 11 (2003), 211-2226, Bioorganic & Chemistry Letters (1999), 2667-2672 and Nucleic Acids Research, 43, (2015), 2993-3011.

Oligonucleotide derivatives of the invention having the partial structures represented by formula (3) and formula (4)

can be easily manufactured by using various kinds of the nucleoside derivatives represented by formula (1) or formula (2) as amidite agents and the like. That is, an oligonucleotide derivative of the invention can be synthesized with a known DNA synthesizer from such a nucleoside derivative, the resulting oligonucleotide derivative can be purified with a column, and the purity of the product can be analyzed by reverse-phase HPLC or MALDI-TOF-MS to obtain the oligonucleotide derivative in purified form. Methods for making the oligonucleotide derivative into an acid-addition salt are well known to those skilled in the art.

Because the oligonucleotide derivative has a specific N-containing group at the ribose 5' position via a linking group, the net charge of RNA can be controlled, fat solubility (Van der Waals intermolecular force) can be increased, and the dsRNA melting temperature can be reduced while sufficiently maintaining RNA functions such as RNA interference in vivo. It is thus possible to improve both ribonuclease resistance and cell membrane permeability. It is also possible to neutralize minus charge derived from phosphate groups and the like, and adjust the overall charge.

At least one of this partial structure may be provided in the oligonucleotide derivative of the invention, or two of the partial structure may be provided for example. By providing a plurality of these partial structures, it is possible to effectively improve or regulate cell membrane permeability, ribonuclease resistance and the like. The oligonucleotide derivative of the invention may also be provided with at least 3 of these partial structures.

The site provided with 1 or 2 or more of the partial structures in the oligonucleotide derivative is not particularly limited, and may be either the 5' end, or the 3' end, or both. The 5' end and 3' end are regions encompassing suitable numbers of nucleotides extending from each end of the polymer chain of the oligonucleotide, and are each regions consisting of not more than 30% for example of the total constituent units of the polymer chain. The percentage of the range from each end differs depending on the total length of the polymer chain, and may not more than 25%, or not more than 20%, or not more than 10%, or not more than 5% for example. More specifically, the 5' end and 3' end may be regions of constituent units derived from 1 to 30, or 1 to 25, or 1 to 20, or 1 to 15, or 1 to 10, or 1 to 8, or 1 to 6, or 1 to 5, or 1 to 4, or 1 to 3, or 1 to 2 nucleoside derivatives for example at each end of the oligonucleotide. The oligonucleotide derivative may be provided with 1 or 2 or more of the partial structures in either of these end regions, with 2 or more being preferred. Moreover, the oligonucleotide derivative may be provided with the partial structures at either the 5' end, or the 3' end (that is, as the first constituent unit from each end) or both.

In the oligonucleotide derivative, 1 or 2 or more of the partial structure may also be provided in the center, which is a part other than the 5' end and 3' end. Ribonuclease resistance and cell membrane permeability are even easier to improve or regulate when the oligonucleotide derivative is provided with the partial structure in the center. It also becomes easier to regulate the charge of the oligonucleotide as a whole.

The oligonucleotide derivative may also be provided with the partial structure in the center and in either or both of the 5' end and 3' end. Preferably, it may be provided with 1 or 2 or more of the partial structure at all of the 5' end, the 3' end, and the center. By thus distributing the partial structure more or less uniformly overall, it is possible to improve the ribonuclease resistance and cell membrane permeability as well as the charge control properties. Providing 2 or more of the partial structure in the center of the oligonucleotide derivative is useful for improving the characteristics.

A partial structure derived from the ribonucleoside derivative represented by formula (3) or a partial structure derived from the deoxyribonucleotide derivative represented by formula (4) may be used as the partial structure in the oligonucleotide derivative. The ribonucleoside derivative represented by formula (3) and the partial structure of formula (4) can be used as substitutes for ribonucleoside derivatives because they comprise an RNA base (uracil (U) or the like) as the B base.

From the standpoint of ribonuclease resistance and cell membrane permeability as well as charge control, $R^4$ in formula (3) and formula (4) preferably has $NHR^7$ with an alkylene having 1 or 2 or more carbon atoms as a linking group in the partial structure. In this case, $R^7$ may be a hydrogen atom or an acyl group having a roughly $C_{1-6}$ alkyl group. This alkylene group may be an ethylene group, propylene group, butylene group, pentylene group or hexylene group or the like. It may also be an ethylene group, propylene group, butylene group or the like for example. It may also be an ethylene group, propylene group or the like for example. By using an ethylene group or propylene group as a linking group, it is possible to obtain greater ribonuclease resistance, cell membrane permeability and charge control properties than are obtained using a methylene group.

The partial structure may also be an amidino group, azide group or guanidino group provided with a linking group. With such a functional group, it is possible to obtain high ribonuclease resistance and cell membrane permeability. In this case, the linking group may be an alkylene group with 1 or more carbon atoms.

In the partial structure, the linking group of $R^4$ in formula (3) and formula (4) is preferably a roughly $C_{1-6}$ alkyl group, and the lower limit of the carbon number is preferably at least 2, or more preferably at least 3. This structure is effective for obtaining ribonuclease resistance and cell membrane permeability.

The oligonucleotide derivative is preferably provided with at least 6 of the partial structure. Having 6 or more is effective for obtaining ribonuclease resistance and cell membrane permeability, as well as charge control properties.

The oligonucleotide derivative may be used for example as siRNA. That is, an oligonucleotide derivative forming a double strand can form complexes with in vivo components (RISC proteins) and sequence-specifically cleave mRNA, so that the information on the mRNA can no longer be translated into specific proteins by ribosomes. It is also thought that it can be incorporated as a constituent of miRNA or as a constituent of aptamer RNA, thus be used while simultaneously providing the features of improved ribonuclease resistance and cell membrane permeability. It can also link to other compounds to form conjugates. Moreover, the oligonucleotide derivative can also be used as a constituent of ribozymes. Furthermore, the oligonucleotide derivative is useful in reagents such as RNA chips.

Thus, because it has properties not found in natural nucleotides, the oligonucleotide derivative is expected to be more useful than natural nucleotides as a component of various RNA drugs that treat disease by inhibiting the action of genes, such as anti-tumor agents and anti-viral agents. That is, the oligonucleotide derivative is useful as such an RNA drug, and as a raw material or intermediate reagent. Moreover, the nucleoside derivative is useful as a raw material or intermediate of such RNA drugs.

The charge control properties, ribonuclease resistance, cell membrane permeability and charge control ability of the oligonucleotide derivative and the biological activity of various kinds of RNA containing the oligonucleotide derivative can be easily evaluated by a person skilled in the art with reference to Embodiments below and to well-known methods at the time of the application.

EXAMPLES

Embodiments are described below as specific examples for explaining the disclosures of the Description in detail. The following Embodiments are for purposes of explaining the disclosures of the Description, and do not limit its scope.

First Embodiment (1) Synthesis of 2'OCH$_3$-5' Aminopropyl Amidite Unit and Resin A 2'OCH$_3$-5' aminopropyl amidite unit and resin were synthesized according to the following scheme.

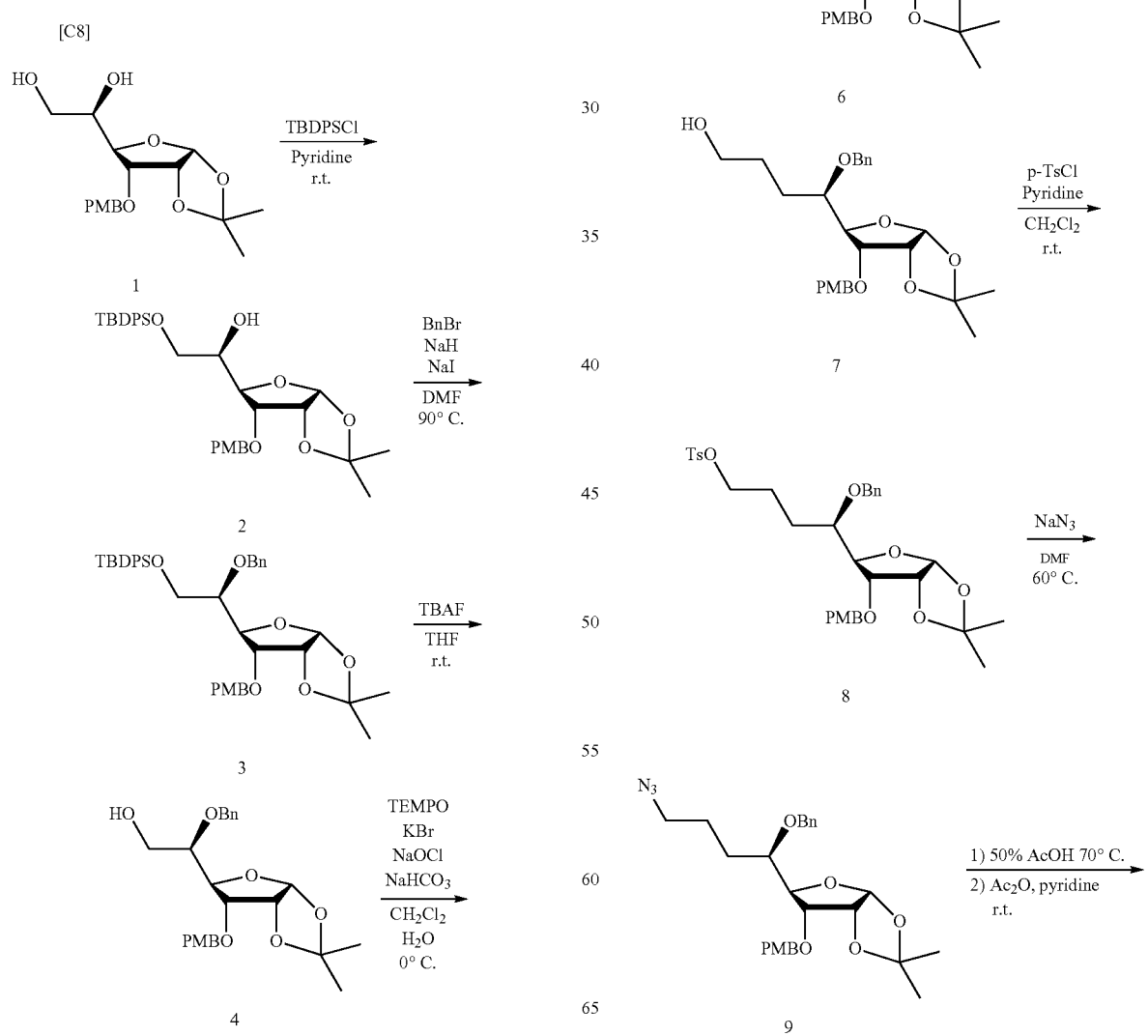

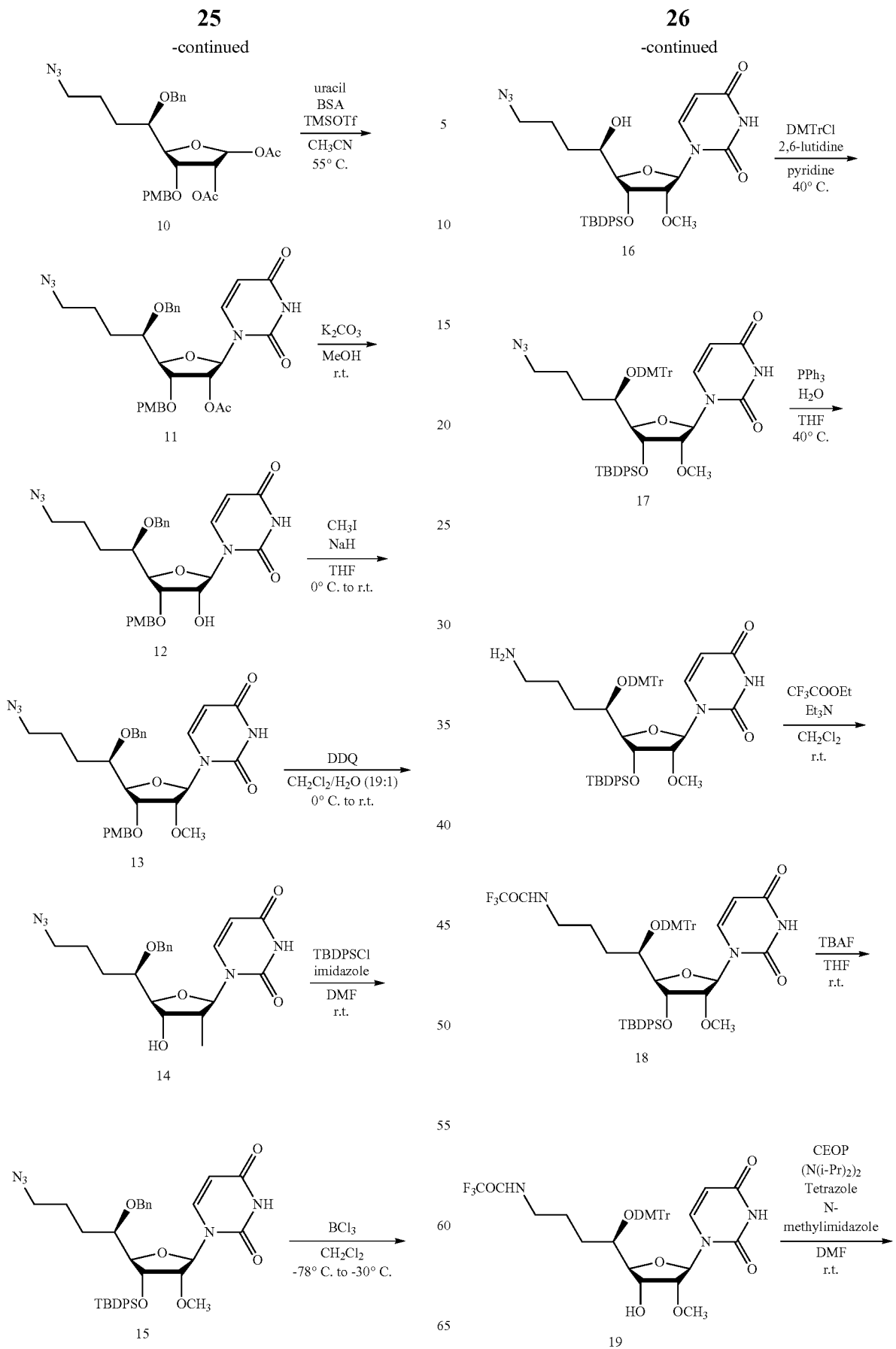

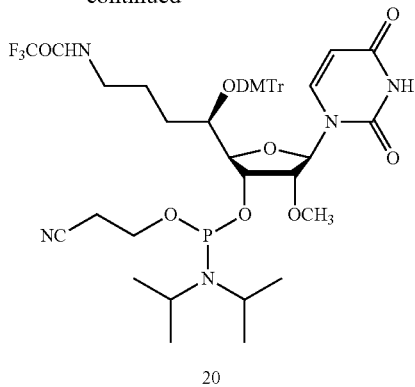

20

1, 2-O-isopropylidene-3-O-(4-methoxybenzyl)-α-D-allofuranose (1)

A target substance 1 was synthesized by known methods (Bioorganic & Medical Chemistry 11 (2003), 211-2226, Bioorganic & Chemistry Letters (1999), 2667-2672) using glucose as a starting material.

6-O-[(1, 1-dimethylethyl)diphenylsilyl]-1, 2-O-isopropylidene-3-O-(4-methoxybenzyl)-α-D-allofuranose (2)

7.25 g (21.3 mmol) of the compound (1) were dissolved in 72 ml of pyridine in an Ar atmosphere, and 6.09 ml (23.4 mmol) of TBDPSCl were added and stirred for 16 hours and 30 minutes at room temperature. The product was extracted from the reaction solution with EtOAc and sat. NaHCO$_3$ aq., and the organic layer was washed with distilled water and sat. NaCl aq. and dried with Na$_2$SO$_4$. The solvent was distilled off under reduced pressure, and the residue was purified by silica gel column chromatography (Hexane:EtOAc=3:1) to obtain a colorless oily compound (2) (11.34 g, 19.6 mmol, 92%).

$^1$H NMR (600 MHz, CDCl$_3$) δ: 7.69-7.65 (m, 4H), 7.44-7.35 (m, 6H), 7.19-7.17 (m, 2H), 6.81-6.80 (m, 2H), 5.71 (d, J=4.2 Hz, 1H), 4.58 (d, J=11 Hz, 1H), 4.48 (t, J=4.1 Hz, 1H), 4.43 (d, J=11.7 Hz, 1H), 4.06 (dd, J=8.6 Hz, 3.4 Hz, 1H), 4.02-4.04 (m, 1H), 3.89 (dd, J=8.6 Hz, 4.8 Hz, 1H), 3.79 (s, 3H), 3.75-3.73 (m, 2H), 2.55 (d, J=3.5 Hz, 1H), 1.55 (s, 3H), 1.34 (s, 3H), 1.06 (s, 9H); $^{13}$C NMR (151 MHz, CDCl$_3$) δ 159.5, 135.8, 135.7, 129.9, 129.9, 129.8, 127.9, 113.9, 113.0, 104.2, 78.0, 77.9, 77.3, 72.1, 71.9, 64.7, 55.4, 27.0, 27.0, 26.7, 19.4; HRMS (ESI) m/z Calcd for C$_{33}$H$_{42}$NaO$_7$Si (M+Na)$^+$; 601.25975 found 601.25809

5-O-Benzyl-6-O-[(1,1-dimethylethyl)diphenylsilyl]-1, 2-O-isopropylidene-3-O-(4-methoxybenzyl)-α-D-allofuranose (3)

11.34 g (19.6 mmol) of the compound (2) were dissolved in 113 ml of DMF in an Ar atmosphere, and 1.57 g (39.2 mmol) of NaH were added and stirred for 30 minutes at room temperature. This was cooled with an ice bath, 4.66 ml (39.2 mmol) of BnBr and 0.59 g (3.92 mmol) of NaI were added, and the mixture was returned to room temperature and then stirred for five hours at 90° C. After five hours, this was cooled with an ice bath, and stirred for 20 minutes after addition of 10 ml of MeOH. The product was extracted from the reaction solution with EtOAc and sat. NaHCO$_3$ aq., and the organic layer was washed with sat. NaCl aq. and dried with Na$_2$SO$_4$. The solvent was distilled off under reduced pressure, and the residue was purified by silica gel column chromatography (Hexane:EtOAc=7:1) to obtain a yellow oily compound (3) (8.69 g, 13.0 mmol, 66%).

$^1$H NMR (600 MHz, CDCl$_3$) δ: 7.68-7.64 (m, 4H), 7.44-7.39 (m, 2H), 7.35-7.31 (m, 5H), 7.30-7.26 (m, 5H), 7.12-7.10 (m, 2H), 6.76-6.74 (m, 2H), 5.67 (d, J=4.1 Hz, 1H), 4.47 (d, J=11.6 Hz, 1H), 4.68 (d, J=11.6 Hz, 1H), 4.54 (d, J=11.6 Hz, 1H), 4.47 (t, J=4.1 Hz, 1H), 4.38 (d, J=11.0 Hz, 1H), 4.26 (dd, J=8.2 Hz, 2.1 Hz, 1H), 4.00-3.96 (m, 2H), 3.80-3.79 (m, 2H), 3.78 (s, 3H), 1.57 (s, 3H), 1.34 (s, 3H), 1.04 (s, 9H); $^{13}$C NMR (151 MHz, CDCl$_3$) δ: 159.4, 139.3, 135.8, 135.8, 133.7, 133.6, 129.9, 129.7, 128.3, 127.8, 127.8, 127.6, 127.4, 113.8, 113.0, 104.2, 79.6, 78.0, 74.1, 71.7, 64.1, 55.4, 27.1, 27.0, 26.8, 19.3, 14.3; HRMS (ESI) m/z Calcd for C$_{40}$H$_{48}$NaO$_7$Si (M+Na)$^+$; 691.30670 found 691.30739

5-O-Benzyl-1, 2-O-isopropylidene-3-O-(4-methoxybenzyl)-α-D-allofuranose (4)

3.67 g (5.49 g) of the compound (3) were dissolved in 37 ml of THF in an Ar atmosphere, 1 M TBAF (8.24 mmol) was added, and the mixture was stirred for 19 hours at room temperature. A product was extracted from the reaction solution with EtOAc and distilled water, and the organic layer was washed with sat. NaCl aq. and dried with Na$_2$SO$_4$. The solvent was distilled off under reduced pressure, and the residue was purified by silica gel column chromatography (Hexane:EtOAc=3:1) to obtain a clear oily compound (4) (2.11 g, 4.91 mmol, 89%).

$^1$HNMR (600 MHz, CDCl3) δ: 7.34-7.32 (m, 2H), 7.30-7.28 (m, 5H), 6.88-6.86 (m, 2H), 5.72 (d, J=4.1 Hz, 1H), 4.72 (d, J=12.4 Hz, 1H), 4.70 (d, J=11.0 Hz, 1H), 4.64 (d, J=11.7 Hz, 1H), 4.56 (t, J=3.42, 1H), 4.50 (d, J=11.7 Hz, 1H), 4.21 (dd, J=8.94 Hz, 2.04 Hz, 1H), 4.03 (dd, J=8.9 Hz, 4.1 Hz, 1H), 3.89-3.87 (m, 1H), 3.80 (s, 3H), 3.67-3.65 (m, 2H), 2.42 (t, J=5.5 Hz, 1H), 1.59 (s, 1H), 1.36 (s, 1H); $^{13}$C NMR (151 MHz, CDCl$_3$) δ: 159.6, 138.5, 129.9, 128.9, 128.3, 127.6, 127.5, 113.8, 112.9, 104.0, 80.0, 77.9, 77.2, 76.3, 73.3, 71.7, 61.9, 55.2, 26.8, 26.5; HRMS (ESI) m/z Calcd for C$_{24}$H$_{30}$NaO$_7$ (M+Na)$^+$; 453.18892 found 453.18636.

(R)-5-O-Benzyl-5-C-[2-ethoxycarbonyl-(E)-vinyl]-1, 2-O-isopropylidene-3-O-(4-methoxybenzyl)-α-D-ribose (5)

4.47 g (10.4 mmol) of the compound (4) were dissolved in 17.3 ml of CH$_2$Cl$_2$ and cooled with an ice bath. 16 mg (0.10 mmol) of TEMPO and 0.5 ml of 2 M KBr aq. were added, and the mixture was stirred in an ice bath. 0.15 g of NaHCO$_3$ were dissolved in 8.5 ml of NaClO aq. and added to the reaction solution, which was then stirred for 40 minutes in an ice bath. The reaction solution was partitioned between CHCl$_3$ and distilled water, and the organic layer was washed with 10% HCl aq., 10% Na$_2$S$_2$O$_3$ aq., distilled water and sat. NaCl aq. and then dried with Na$_2$SO$_4$. The solvent was distilled off under reduced pressure. The resulting residue was dissolved in 2.43 ml of (EtO)$_2$P(O)CH$_2$COOEt in 25 ml of THF in an Ar atmosphere, 0.49 g of NaH was added, and the mixture was stirred for 10 minutes in an ice bath. The residue dissolved in 25 ml of THF was added dropwise and stirred for 30 minutes at room temperature. 30 ml of distilled water was added and stirred at room temperature. The product was extracted from the reaction solution with EtOAc and distilled water, and the organic layer was washed with sat. NaCl aq. and dried with $Na_2SO_4$. The solvent was distilled off under reduced pressure, and the residue was purified by silica gel column chromatography (Hexane:EtOAc=3:1) to obtain a yellow oily compound (5) (4.15 g, 8.33 mmol, 80%).

$^1$H NMR (600 MHz, $CDCl_3$) δ 7.34-7.32 (m, 2H), 7.29-7.27 (m, 3H), 7.23-7.22 (m, 2H), 6.86-6.83 (m, 3H), 5.88 (d, J=13.7 Hz, 1H), 5.71 (d, J=4.1 Hz, 1H), 4.63 (d, J=11.7 Hz, 1H), 4.62 (d, J=11.6 Hz, 1H), 4.50 (m, 2H), 4.21 (d, J=11.6 Hz, 1H), 4.26-4.22 (m, 2H), 4.19 (q, J=6.9 Hz, 2H), 3.82-3.80 (m, 1H), 3.80 (s, 3H), 1.58 (s, 3H), 1.35 (s, 3H), 1.29 (t, J=7.6 Hz, 3H); $^{13}$C NMR (151 MHz, $CDCl_3$) δ: 165.9, 159.6, 143.6, 138.0, 130.0, 129.6, 128.5, 127.8, 127.8, 123.8, 114.0, 113.3, 104.4, 80.8, 77.6, 77.2, 76.6, 72.2, 71.8, 60.6, 55.4, 27.1, 26.8, 14.5; HRMS (ESI) m/z Calcd for $C_{28}H_{34}NaO_8$ (M+Na)$^+$; 521.21514 found 521.21582.

(R)-5-O-Benzyl-5-C-[2-ethoxycarbonylethyl]-1, 2-O-isopropylidene-3-O-(4-methoxybenzyl)-α-D-ribose (6)

5.07 g (10.1 mmol) of the compound (5) were dissolved in 25 ml of EtOAc, 1.45 g (13.6 mmol) of 5% Pd/C and 3.18 g (50.5 mmol) of ammonium formate were added, and the mixture was stirred for 5 hours and 30 minutes at room temperature. The reaction solution was filtered through Celite, and the filtrate was distilled under reduced pressure. The residue was purified by silica gel column chromatography (Hexane:EtOAc=3:1) to obtain a clear oily compound (6) (4.57 g, 9.13 mmol, 90%).

$^1$H NMR (600 MHz, $CDCl_3$) δ: 7.34-7.27 (m, 5H), 7.23-7.22 (m, 2H), 6.85-6.83 (m, 2H), 5.65 (d, J=3.4 Hz, 1H), 4.67 (d, J=11.7 Hz, 1H), 4.65 (d, J=11.7 Hz, 1H), 4.52 (d, J=11.7 Hz, 1H), 4.50 (d, J=11.0 Hz, 1H), 4.48 (t, J=4.1 Hz, 1H), 4.17 (dd, J=8.94 Hz, 2.1 Hz, 1H), 3.94 (dd, J=8.6 Hz, 4.1 Hz, 1H), 3.78 (s, 3H), 3.73-3.70 (m, 1H), 2.42-2.37 (m, 1H), 2.33-2.28 (m, 1H), 1.96-1.90 (m, 1H), 1.80-1.74 (m, 1H), 1.57 (s, 3H), 1.33 (s, 3H), 1.20 (t, J=6.9 Hz, 3H); $^{13}$C NMR (151 MHz, $CDCl_3$) δ: 173.5, 159.5, 138.9, 129.9, 129.8, 128.4, 127.8, 127.5, 113.9, 113.0, 104.0, 81.1, 77.9, 77.3, 77.1, 73.5, 71.9, 60.5, 60.4, 55.4, 31.0, 27.1, 26.8, 26.2, 14.3; HRMS (ESI) m/z Calcd for $C_{28}H_{36}KO_8$ (M+K)$^+$; 539.20472 found 539.20262.

(R)-5-O-Benzyl-5-C-hydroxypropyl-1, 2-O-isopropylidene-3-O-(4-methoxybenzyl)-α-D-ribose (7)

35 ml of THF were added to 0.55 g (14.4 mmol) of $LiAlH_4$ in an ice bath in an Ar atmosphere and stirred. A solution of 3.61 g of the compound (6) dissolved in 10 ml of THF was added dropwise and stirred for 30 minutes in an ice bath. A saturated aqueous solution of (+)-sodium potassium tartrate tetrahydrate was added and stirred for 30 minutes at room temperature. The product was extracted from the reaction solution with EtOAc and distilled water, and the organic layer was washed with sat. NaCl aq. and dried with $Na_2SO_4$. The solvent was distilled off under reduced pressure, and the residue was purified by silica gel column chromatography (Hexane:EtOAc=3:1) to obtain a clear oily compound (7) (3.28 g, 7.14 mmol, 99%).

$^1$H NMR (400 MHz, $CDCl_3$) δ: 7.35-7.27 (m, 7H), 6.87-6.85 (m, 2H), 5.67 (d, J=3.7 Hz, 1H), 4.71 (d, J=11.9 Hz, 1H), 4.68 (d, J=12.8 Hz, 1H), 4.56 (d, J=11.5 Hz, 1H), 4.51 (t, J=4.1 Hz, 1H), 4.49 (d, J=11.0 Hz, 1H), 4.20 (dd, J=8.7 Hz, 1.8 Hz, 1H), 3.96 (dd, J=8.7 Hz, 4.6 Hz, 1H), 3.80 (s, 3H), 3.72-3.69 (m, 1H), 3.57-3.53 (m, 1H), 1.70-1.63 (m, 2H), 1.59 (s, 3H), 1.56-1.52 (m, 1H), 1.45-1.42 (m, 1H), 1.36 (s, 3H); $^{13}$C NMR (101 MHz, $CDCl_3$) δ: 159.5, 138.9, 129.9, 129.8, 128.4, 127.9, 127.6, 113.9, 113.0, 104.0, 88.2, 78.2, 77.9, 77.0, 73.5, 71.8, 62.8, 55.4, 29.6, 27.4, 27.1, 26.8; HRMS (ESI) m/z Calcd for $C_{26}H_{34}NaO_7$ (M+Na)$^+$; 481.22022 found 481.22082.

(R)-5-O-Benzyl-1, 2-O-isopropylidene-3-O-(4-methoxybenzyl)-5-C-p-toluenesulfonyloxypropyl-α-D-ribose (8)

0.10 g (0.23 mmol) of the compound (7) were dissolved in 1.0 ml of $CH_2Cl_2$ in an Ar atmosphere and stirred in an ice bath. 0.15 g of p-TsCl and 0.13 ml of pyridine were added, and the mixture was stirred for three hours at room temperature. The product was extracted from the reaction solution with $CHCl_3$ and sat. $NaHCO_3$ aq., and the organic layer was washed with sat. NaCl aq. and dried with $Na_2SO_4$. The solvent was distilled off under reduced pressure, and the residue was purified by silica gel column chromatography (Hexane:EtOAc=3:1) to obtain a clear oily compound (8) (0.13 g, 0.217 mmol, 96%).

$^1$H NMR (600 MHz, $CDCl_3$) δ: 7.74 (d, J=8.3 Hz, 2H), 7.32-7.27 (m, 5H), 7.25-7.21 (m, 4H), 6.88-6.85 (m, 2H), 5.65 (d, J=4.1 Hz, 1H), 4.64 (d, J=11.7 Hz, 2H), 4.50 (t, J=4.1 Hz, 1H), 4.46 (d, J=11.6 Hz, 1H), 4.46 (d, J=12.4 Hz, 1H), 4.10 (dd, J=6.5 Hz, 2.1 Hz, 1H), 3.94-3.87 (m, 3H), 3.81 (s, 3H), 3.59-3.58 (m, 1H), 2.42 (s, 3H), 1.82-1.74 (m, 1H), 1.64-1.59 (m, 2H), 1.56 (s, 3H), 1.47-1.42 (m, 1H), 1.35 (s, 3H); $^{13}$C NMR (101 MHz, $CDCl_3$) δ: 159.6, 144.8, 138.8, 133.2, 129.9, 129.9, 129.7, 128.4, 128.0, 127.8, 127.6, 113.9, 113.0, 104.0, 81.1, 77.8, 77.4, 77.0, 73.4, 71.8, 70.6, 60.5, 55.4, 27.1, 26.9, 26.8, 25.7, 21.8, 21.2, 14.3; HRMS (ESI) m/z Calcd for $C_{33}H_{40}NaO_9S$ (M+Na)$^+$; 635.22907 found 635.22816.

(R)-5-C-Azidopropyl-5-O-benzyl-1, 2-O-isopropylidene-3-O-(4-methoxybenzyl)-α-D-ribose (9)

4.10 g (6.70 mmol) of the compound (8) were dissolved in 40 ml of DMF in an Ar atmosphere, and 3.65 g (56.2 mmol) of $NaN_3$ were added and stirred at 60° C. The product was extracted from the reaction solution with EtOAc and sat. NaCl aq., and the organic layer was washed with sat. NaCl aq. and dried with $Na_2SO_4$. The solvent was distilled off under reduced pressure, and the residue was purified by silica gel column chromatography (Hexane:EtOAc=5:1) to obtain a clear oily compound (9) (2.63 g, 5.43 mmol, 81%).

$^1$H NMR (600 MHz, $CDCl_3$) δ: 7.34-7.27 (m, 7H), 6.88-6.85 (m, 2H), 5.68 (d, J=3.4 Hz, 1H), 4.70 (d, J=11.6 Hz, 1H), 4.67 (d, J=11.7 Hz, 1H), 4.54 (d, J=11.7 Hz, 1H), 4.52 (t, J=4.1 Hz, 1H), 4.49 (d, J=11.6 Hz, 1H), 4.17 (dd, J=8.6 Hz, 1.4 Hz, 1H), 3.96 (dd, J=8.6 Hz, 4.8 Hz, 1H), 3.80 (s, 3H), 3.70-3.68 (m, 1H), 3.17 (t, J=6.8 Hz, 2H), 1.75-1.64 (m, 2H), 1.59 (s, 3H), 1.53-1.46 (m, 2H), 1.36 (s, 3H); $^{13}$C NMR (151 MHz, $CDCl_3$) δ: 159.6, 138.9, 129.9, 129.8, 128.4, 127.9, 127.6, 113.9, 113.0, 104.0, 81.2, 77.9, 77.5, 77.1, 73.5, 71.8, 55.4, 51.5, 28.2, 27.1, 26.8, 25.7; HRMS (ESI) m/z Calcd for $C_{26}H_{33}N_3NaO_6$(M+Na)$^+$; 506.22670 found 506.22941.

(R)-5-C-Azidopropyl-5-O-benzyl-1, 2-O-di-acetyl-3-O-(4-methoxybenzyl)-α-D-ribose (10)

The compound (9) was dissolved in a 50% aqueous acetic acid solution, and stirred for 24 hours at 70° C. EtOH was added, the solvent was distilled off under reduced pressure, and the residue was purified by silica gel column chromatography (Hexane:EtOAc=1:1) to obtain a clear oily compound (2.07 g, 4.67 mmol, 60%). This compound was dissolved in 10.1 ml of pyridine in an Ar atmosphere, 6.7 ml (72.4 mmol) of $Ac_2O$ were added, and the mixture was stirred for six hours at room temperature. The reaction solution was cooled with an ice bath and placed in ice water. The reaction solution was extracted with EtOAc and distilled water, and the organic layer was washed with sat. $NaHCO_3$ aq. and sat. NaCl aq. and dried with $Na_2SO_4$. The solvent was distilled off under reduced pressure, and the residue was purified by silica gel column chromatography (Hexane:EtOAc=4:1) to obtain a compound (10) (6.49 g, 10.5 mmol, 97%).

$^1$H NMR (600 MHz, $CDCl_3$) δ: 7.36-7.27 (m, 5H), 7.20 (d, J=8.3 Hz, 2H), 6.86-6.85 (m, 2H), 6.11 (s, 1H), 5.33 (d, J=4.8 Hz, 1H), 4.71 (d, J=11.7 Hz, 1H), 4.55 (d, J=11.7 Hz, 1H), 4.53 (d, J=10.3 Hz, 1H), 4.41 (d, J=10.3 Hz, 1H), 4.40 (dd, J=8.3 Hz, 4.8 Hz, 1H), 4.15 (dd, J=2.8 Hz, 7.6 Hz, 1H), 3.80 (s, 3H), 3.67-3.65 (m, 1H), 3.18-3.15 (m, 2H), 2.13 (s, 3H), 1.85 (s, 3H), 1.70-1.50 (m, 4H); $^{13}$C NMR (151 MHz, $CDCl_3$) δ: 170.0, 169.5, 159.7, 130.1, 129.4, 128.5, 127.7, 127.6, 114.0, 98.6, 83.8, 77.5, 75.9, 74.0, 73.1, 73.0, 55.4, 51.5, 28.0, 25.3, 21.0, 20.9; HRMS (ESI) m/z Calcd for $C_{27}H_{33}N_3NaO_8$ $(M+Na)^+$; 550.21653 found 550.21745.

2'-O-Acetyl-(R)-5'-C-azidopropyl-5'-O-benzyl-3'-O-(4-methoxybenzyl)-uridine (11)

2.04 g (3.87 mmol) of the compound (10) and 0.74 g (6.60 mmol) of uracil were dissolved in 20 ml of $CH_3CN$ in an Ar atmosphere, 3.6 ml (13.9 mmol) of BSA were added, and the mixture was stirred for one hour at 55° C. This was cooled in an ice bath, 1.6 ml (8.75 mmol) of TMSOTf were added dropwise, and the mixture was returned to room temperature and then stirred for two hours at 55° C. This was cooled in an ice bath, and 25 ml of sat. $NaHCO_3$ aq. were added and stirred. The product was extracted from the reaction solution with EtOAc and sat. NaCl aq., and the organic layer was washed with sat. NaCl aq. and dried with $Na_2SO_4$. The solvent was distilled off under reduced pressure, and the residue was purified by silica gel column chromatography (Hexane:EtOAc=1:1) to obtain a clear foamy compound (11) (2.04 g, 3.51 mmol, 91%).

$^1$H NMR (600 MHz, $CDCl_3$) δ: 8.82 (s, 1H), 7.39-7.29 (m, 7.22 (d, J=8.3 Hz, 2H), 6.88 (d, J=8.2 Hz, 2H), 6.04 (d, J=4.1 Hz, 1H), 5.23 (t, J=5.5 Hz, 1H), 5.18 (dd, J=7.9 Hz, 2.1 Hz, 1H), 4.73 (d, J=11.6 Hz, 1H), 4.53 (d, J=11.0 Hz, 1H), 4.45 (d, J=11.0 Hz, 1H), 4.40 (d, J=11.0 Hz, 1H), 4.30 (t, J=6.2 Hz, 1H), 4.10 (dd, J=5.5 Hz, 2.8 Hz, 1H), 3.81 (s, 3H), 3.75-3.74 (m, 1H), 3.24 (t, J=6.8 Hz, 2H), 2.12 (s, 3H), 1.77-1.72 (m, 1H), 1.66-1.52 (m, 3H); $^{13}$C NMR (151 MHz, $CDCl_3$) δ: 170.1, 162.9, 159.7, 150.2, 140.1, 137.7, 130.0, 129.2, 128.8, 128.3, 127.7, 114.0, 102.7, 87.4, 83.8, 78.4, 74.5, 74.2, 73.0, 72.9, 55.4, 51.4, 27.4, 25.4, 20.9; HRMS (ESI) m/z Calcd for $C_{29}H_{33}KN_5O_8$ $(M+Na)^+$; 618.19662 found 618.19882.

(R)-5'-C-Azidopropyl-5'-O-benzyl-3'-O-(4-methoxybenzyl)-uridine (12)

0.53 g (0.91 mmol) of the compound (11) were dissolved in 5.2 ml of MeOH in an Ar atmosphere, 0.38 g (2.75 mmol) of $K_2CO_3$ were added, and the mixture was stirred for one hour. The product was extracted from the reaction solution with EtOAc and distilled water, and the organic layer was washed with sat. NaCl aq. and dried with $Na_2SO_4$. The solvent was distilled off under reduced pressure, and the residue was purified by silica gel column chromatography (Hexane:EtOAc=1:2) to obtain a white solid compound (12) (0.46 g, 0.86 mmol, 95%).

$^1$H NMR (400 MHz, $CDCl_3$) δ: 8.04 (s, 1H), 7.40-7.34 (m, 3H), 7.29-7.27 (m, 3H), 7.25-7.21 (m, 2H), 6.91-6.89 (m, 2H), 5.85 (d, J=5.5 Hz, 1H), 5.26 (dd, J=8.3 Hz, 2.3 Hz, 1H), 4.74 (d, J=11.0 Hz, 1H), 4.60 (d, J=11.4 Hz, 1H), 4.53 (d, J=11.0 Hz, 1H), 4.41 (d, J=1H), 4.17-4.07 (m, 3H), 3.82 (s, 3H), 3.71-3.69 (m, 1H), 3.29-3.27 (m, 2H), 2.87 (d, J=7.3 Hz, 1H), 1.78-1.59 (m, 4H); $^{13}$C NMR (151 MHz, $CDCl_3$) δ: 163.0, 159.9, 150.6, 140.3, 137.7, 130.0, 128.8, 128.7, 128.3, 127.7, 114.2, 102.7, 89.4, 83.7, 78.8, 75.9, 73.5, 72.8, 72.6, 55.4, 51.5, 27.5, 25.2; HRMS (ESI) m/z Calcd for $C_{28}H_{33}N_5NaO_7$ $(M+Na)^+$; 560.21212 found 560.21286.

(R)-5'-C-Azidopropyl-5'-O-benzyl-3'-O-(4-methoxybenzyl)-2'-O-methyl-uridine (13)

0.46 g (0.86 mmol) of the compound (12) were dissolved in 4.6 ml of THF in an Ar atmosphere, this was cooled in an ice bath, 0.10 g (2.55 mmol) of NaH were added, and the mixture was stirred for five minutes in an ice bath. This was shaded from light with aluminum foil as 0.27 ml (4.34 mmol) of $CH_3I$ were added dropwise, and the mixture was stirred for four hours in an ice bath. This was then stirred for three hours at room temperature. A small amount of sat. $NaHCO_3$ aq. was added and stirred at room temperature. The product was extracted from the reaction solution with EtOAc and sat. $NaHCO_3$ aq., and the organic layer was washed with sat. NaCl aq. and dried with $Na_2SO_4$. The solvent was distilled off under reduced pressure, and the residue was purified by silica gel column chromatography (Hexane:EtOAc=2:3) to obtain a clear foamy compound (13) (0.43 g, 0.78 mmol, 90%).

$^1$H NMR (600 MHz, $CDCl_3$) δ: 8.31 (s, 1H), 7.55 (d, J=7.5 Hz, 1H), 7.39-7.33 (m, H), 5.94 (d, J=2.1 Hz, 1H), 4.96 (dd, J=8.3 Hz, 2.1 Hz, 1H), 4.77 (d, J=11.0 Hz, 1H), 4.56 (d, J=11.6 Hz, 1H), 4.49 (d, J=11.0 Hz, 1H), 4.41 (d, J=11.0 Hz, 1H), 4.21 (dd, J=7.2 Hz, 2.8 Hz, 1H), 4.11 (dd, J=7.2 Hz, 4.8 Hz, 1H), 3.83-3.82 (m, 1H), 3.82 (s, 3H), 3.64 (dd, J=4.8 Hz, 2.8 Hz, 1H), 3.31-3.24 (m, 2H), 1.88-1.83 (m, 1H), 1.72-1.65 (m, 3H); $^{13}$C NMR (151 MHz, $CDCl_3$) δ: 163.4, 159.7, 150.1, 140.3, 137.7, 129.9, 129.2, 128.8, 128.3, 127.7, 114.0, 102.0, 87.9, 82.5, 82.5, 78.2, 73.9, 72.6, 58.6, 55.4, 51.5, 27.1, 25.3; HRMS (ESI) m/z Calcd for $C_{28}H_{33}N_5NaO_7$ $(M+Na)^+$; 574.22777 found 574.22525.

(R)-5'-C-Azidopropyl-5'-O-benzyl-2'-O-methyl-uridine (14)

0.43 g (0.78 mmol) of the compound (13) were dissolved in 1.85 ml of $CH_2Cl_2$ in an Ar atmosphere, 96 μl of distilled water were added, and the mixture was cooled in an ice bath. 0.21 g (0.94 mmol) of DDQ were added and stirred for two hours in an ice bath. This was then stirred for two hours at room temperature. 5 ml of sat. $NaHCO_3$ aq. were added and stirred at room temperature. The reaction solution was filtered through Celite, the product was extracted from the filtrate with $CHCl_3$ and sat. NaCl aq., and the organic layer was dried with $Na_2SO_4$. The solvent was distilled off under reduced pressure, and the residue was purified by silica gel column chromatography (Hexane:EtOAc=1:2) to obtain a white solid compound (14) (0.27 g, 0.62 mmol, 79%).

$^1$H NMR (600 MHz, $CDCl_3$) δ: 8.33 (s, 1H), 7.57 (d, J=8.3 Hz, 1H), 7.41-7.32 (m, 5H), 5.96 (d, J=2.3 Hz, 1H), 4.98 (dd, J=8.2 Hz, 2.3 Hz, 1H), 4.81 (d, J=11.0 Hz, 1H), 4.45 (d, J=11.0 Hz, 1H), 4.41-4.36 (m, 1H), 3.99 (dd, J=6.9 Hz, 2.3 Hz, 1H), 4.01-3.97 (m, 1H), 3.63 (dd, J=5.5 Hz, 2.3 Hz, 1H), 3.58 (s, 3H), 3.34 (t, J=6.9 Hz, 2H), 2.75 (d, J=8.2 Hz, 1H), 1.96-1.68 (m, 4H); $^{13}$C NMR (151 MHz, CDCl$_3$) δ: 163.3, 150.2, 140.0, 137.6, 128.8, 128.3, 127.8, 102.2, 86.7, 84.7, 84.2, 78.3, 72.9, 67.8, 58.8, 51.5, 27.2, 25.4; HRMS (ESI) m/z Calcd for C$_{20}$H$_{25}$N$_5$NaO$_6$(M+Na)$^+$; 454.17025 found 454.16755.

(R)-5'-C-Azidopropyl-5'-O-benzyl-3'-O-[(1, 1-dimethylethyl)diphenylsilyl]-2'-O-methyl-uridine (15)

0.27 g (0.62 mmol) of the compound (14) were dissolved in 2.7 ml of DMF in an Ar atmosphere, 0.42 g (6.17 mmol) of imidazole and 0.80 ml (3.08 mmol) of TBDPSCl were added, and the mixture was stirred for 18 hours at room temperature. The product was extracted from the reaction solution with EtOAc and distilled water, and the organic layer was washed with sat. NaHCO$_3$ aq. and sat. NaCl aq. and dried with Na$_2$SO$_4$. The solvent was distilled off under reduced pressure, and the residue was purified by silica gel column chromatography (Hexane:EtOAc=3:2) to obtain a white foamy compound (15) (0.39 g, 0.59 mmol, 95%).

$^1$H NMR (600 MHz, CDCl$_3$) δ: 7.91 (s, 1H), 7.73-7.71 (m, 2H), 7.67-7.66 (m, 2H), 7.44 (t, J=7.6 Hz, 2H), 7.39-7.33 (m, 8H), 7.23-7.22 (m, 2H), 5.88 (d, J=3.5 Hz, 1H), 4.94 (dd, J=8.2 Hz, 2.8 Hz, 1H), 4.74 (d, J=11.9 Hz, 1H), 4.41 (dd, J=6.2 Hz, 4.8 Hz, 1H), 4.38 (d, J=11.0 Hz, 1H), 4.22 (dd, J=6.2 Hz, 2.1 Hz, 1H), 3.74-3.72 (m, 1H), 3.24-3.15 (m, 2H), 3.10 (dd, J=4.8 Hz, 3.4 Hz, 1H), 3.07 (s, 3H), 1.80-1.75 (m, 1H), 1.64-1.56 (m, 3H), 1.09 (s, 9H); $^{13}$C NMR (151 MHz, CDCl$_3$) δ: 163.1, 149.9, 140.1, 137.7, 136.2, 136.0, 133.0, 130.2, 130.2, 128.8, 128.2, 127.9, 127.8, 127.5, 101.9, 86.5, 84.1, 83.3, 78.7, 72.7, 69.9, 57.6, 51.3, 27.1, 27.1, 25.8, 19.5; HRMS (ESI) m/z Calcd for C$_{36}$H$_{43}$KN$_5$O$_6$Si(M+K)$^+$; 708.26197 found 708.26246.

(R)-5'-C-Azidopropyl-3'-O-[(1, 1-dimethylethyl)diphenylsilyl]-2'-O-methyl-uridine (16)

0.39 g (0.59 mmol) of the compound (15) were dissolved in 6.0 ml of CH$_2$Cl$_2$ in an Ar atmosphere, and stirred for 10 minutes at −78° C. 3.5 ml (3.5 mmol) of 1 M BCl$_3$ were added and stirred for three hours at −78° C. The temperature was raised to −30° C., 10 ml of a mixed 1:1 (v/v) solution of CH$_2$Cl$_2$:MeOH were added, and the mixture was stirred for 10 minutes. This was further stirred at room temperature, the product was extracted with CHCl$_3$ and sat. NaHCO$_3$ aq., and the organic layer was washed with sat. NaCl aq. and dried with Na$_2$SO$_4$. The solvent was distilled off under reduced pressure, and the residue was purified by silica gel column chromatography (Hexane:EtOAc=1:2) to obtain a white foamy compound (16) (0.34 g, 0.58 mmol, 99%).

$^1$H NMR (600 MHz, CDCl$_3$) δ: 8.09 (s, 1H), 7.73-7.72 (m, 2H), 7.68-7.66 (m, 2H), 7.42-7.38 (m, 5H), 5.73 (dd, J=8.3 Hz, 2.1 Hz, 1H), 5.55 (d, J=6.9 Hz, 1H), 4.35 (dd, J=4.8 Hz, 2.0 Hz, 1H), 4.09 (dd, J=6.9 Hz, 4.8 Hz, 1H), 4.00 (t, J=2.1 Hz, 1H), 3.66-3.62 (m, 1H), 3.54 (d, J=2.1 Hz, 1H), 3.19 (s, 3H), 3.17-3.11 (m, 2H), 1.64-1.60 (m, 1H), 1.46-1.41 (m, 1H), 1.09 (s, 9H), 1.02-0.98 (m, 1H), 0.92-0.88 (m, 1H); $^{13}$C NMR (151 MHz, CDCl$_3$) δ: 163.1, 150.4, 143.8, 136.2, 136.1, 133.2, 133.0, 130.3, 130.2, 128.0, 127.8, 102.7, 92.7, 89.9, 81.0, 71.3, 70.2, 58.5, 51.2, 29.4, 27.0, 25.7, 19.5; HRMS (ESI) m/z Calcd for C$_{29}$H$_{37}$N$_5$NaO$_6$Si (M+Na)$^+$; 602.24108 found 602.23893.

(R)-5'-C-Azidopropyl-5'-O-(4, 4'-dimethoxytrityl)-3'-O-[(1, 1-dimethylethyl)diphenylsilyl]-2'-O-methyl-uridine (17)

0.71 g (1.22 mmol) of the compound (16) were dissolved in 4.1 ml of pyridine in an Ar atmosphere, 2.07 g (6.11 mmol) of DMTrCl and 0.85 ml (7.34 mmol) of 2,6-lutidine were added, and the mixture was stirred for 48 hours at 40° C. The product was extracted from the reaction solution with EtOAc and distilled water, and the organic layer was washed with sat. NaCl aq. and dried with Na$_2$SO$_4$. The solvent was distilled off under reduced pressure, and the residue was purified by silica gel column chromatography (Hexane:EtOAc=3:2) to obtain a yellow foamy compound (17) (0.81 g, 0.92 mmol, 75%).

$^1$H NMR (600 MHz, CDCl$_3$) δ: 7.96 (s, 1H), 7.76-7.75 (m, 2H), 7.72-7.71 (m, 2H), 7.51-7.40 (m, 6H), 6.75 (d, J=8.9 Hz, 4H), 5.93 (d, J=5.5 Hz, 1H), 5.06 (d, J=6.2 Hz, 1H), 4.504.49 (m, 1H), 4.12-4.11 (m, 1H), 3.77 (s, 3H), 3.77 (s, 3H), 3.29-3.27 (m, 2H), 3.04 (s, 3H), 2.83-2.80 (m, 1H), 2.75-2.71 (m, 1H), 1.20-1.13 (m, 1H), 1.10 (s, 9H), 1.03-0.99 (m, 1H); $^{13}$C NMR (151 MHz, CDCl$_3$) δ: 163.3, 158.8, 158.7, 150.2, 146.2, 136.4, 136.0, 135.9, 135.8, 133.5, 133.0, 130.7, 130.4, 130.2, 130.1, 128.1, 127.9, 127.7, 127.0, 113.3, 113.2, 113.1, 102.4, 87.4, 86.4, 84.9, 82.6, 73.7, 70.7, 57.9, 55.3, 55.3, 51.1, 27.8, 27.0, 25.3, 19.5; HRMS (ESI) m/z Calcd for C$_{50}$H$_{55}$KN$_5$O$_8$Si(M+K)$^+$; 920.34570 found 920.34581.

4'-Dimethoxytrityl)-3'-O-[(1, 1-dimethylethyl)diphenylsilyl]-2'-O-methyl-5'-C-trifluoroacetylaminopropyl-uridine (18)

0.17 g (0.19 mmol) of the compound (17) were dissolved in 1.7 ml of THF in an Ar atmosphere, and 0.13 g (0.50 mmol) of Ph$_3$P and 0.15 ml (8.32 mmol) of distilled water were added and stirred for three hours at 40° C. The solvent was distilled off under reduced pressure, the residue was dissolved in 1.65 ml of CH$_2$Cl$_2$, and 40 µl (0.29 mmol) of Et$_3$N and 70 µl (0.59 mmol) of CF$_3$COOEt were added and stirred for 25 hours. The product was extracted from the reaction solution with EtOAc and distilled water, and the organic layer was washed with sat. NaCl aq. and dried with Na$_2$SO$_4$. The solvent was distilled off under reduced pressure, and the residue was purified by silica gel column chromatography (Hexane:EtOAc=3:2) to obtain a yellow foamy compound (18) (0.16 g, 0.17 mmol, 87%).

$^1$H NMR (600 MHz, CDCl$_3$) δ: 7.93 (s, 1H), 7.75-7.74 (m, 2H), 7.70-7.69 (m, 2H), 7.51-7.47 (m, 4H), 7.41 (t, J=7.6 Hz, 4H), 7.28-7.27 (m, 2H), 7.21-7.17 (m, 1H), 6.95 (d, J=8.2 Hz, 1H), 6.74 (d, J=7.6 Hz, 4H), 5.89 (d, J=5.5 Hz, 1H), 5.87 (s, 1H), 5.13 (dd, J=8.2 Hz, 2.0 Hz, 1H), 4.45 (t, J=4.1 Hz, 1H), 4.11 (t, J=3.4 Hz, 1H), 3.77 (s, 3H), 3.76 (s, 3H), 3.31 (t, J=5.5 Hz, 1H), 3.28-3.26 (m, 1H), 3.05 (s, 3H), 2.88-2.84 (m, 2H), 1.30-1.24 (m, 2H), 1.09 (s, 9H), 1.04-0.95 (m, 2H); $^{13}$C NMR (151 MHz, CDCl$_3$) δ: 162.8, 158.9, 158.8, 150.1, 146.1, 140.6, 136.4, 136.1, 135.8, 133.8, 132.8, 130.6, 130.4, 130.3, 130.1, 128.1, 128.0, 127.9, 127.9, 127.1, 113.3, 113.2, 102.5, 87.4, 87.1, 85.2, 82.3, 73.5, 70.7, 58.0, 55.4, 55.4, 39.6, 27.7, 27.0, 25.1, 19.6; HRMS (ESI) m/z Calcd for C$_{52}$H$_{56}$F$_3$KN$_3$O$_9$Si (M+K)$^+$; 990.33750 found 990.33913.

(R)-5'-O-(4, 4'-Dimethoxytrityl)-2'-O-methyl-5'-C-trifluoroacetylaminopropyl-uridine (19)

0.86 g (0.91 mmol) of the compound (18) were dissolved in 8.6 ml of THF in an Ar atmosphere, and 1.4 ml (1.4 mmol)

of 1 M TBAF were added and stirred for six hours at room temperature. The solvent was distilled off under reduced pressure, and the residue was purified by silica gel column chromatography (Hexane:EtOAc=1:2) to obtain a white solid compound (19) (0.55 g, 0.77 mmol, 85%).

$^1$H NMR (600 MHz, CDCl$_3$) δ: 11.41 (d, J=1.4 Hz, 1H), 9.28 (t, J=5.5 Hz, 1H), 7.42 (d, J=7.6 Hz, 2H), 7.31-7.29 (m, 6H), 7.22 (t, J=7.6 Hz, 1H), 6.89 (dd, J=8.9 Hz, 2.1 Hz, 4H), 5.69 (d, J=6.2 Hz, 1H), 5.29 (dd, J=8.3 Hz, 2.0 Hz, 1H), 5.16 (d, J=6.8 Hz, 1H), 4.11 (dd, J=11.0 Hz, 6.2 Hz, 1H), 3.74 (s, 6H), 3.58 (t, J=5.5 Hz, 1H), 3.30-3.29 (m, 1H), 3.27 (s, 3H), 2.92-2.86 (m, 2H), 1.33-1.23 (m, 4H); $^{13}$C NMR (151 MHz, CDCl$_3$) δ:162.8, 158.2, 150.4, 146.3, 140.6, 136.2, 136.1, 130.3, 130.2, 127.9, 127.7, 126.7, 113.0, 102.0, 86.1, 85.7, 84.4, 81.2, 72.7, 67.7, 57.6, 55.0, 55.0, 27.1, 24.2; HRMS (ESI) m/z Calcd for C$_{36}$H$_{38}$F$_3$N$_3$NaO$_9$ (M+Na)$^+$; 736.24578 found 736.24725.

3'-O-[2-Cyanoethoxy(diisopropylamino)phosphino]-(R)-5'-O-(4, 4'-dimethoxytrityl)-2'-O-methyl-5'-C-trifluoroacetylaminopropyl-uridine (20)

0.19 g (0.27 mmol) of the compound (19) were dissolved in 1.5 ml of DMF in an Ar atmosphere, 17 mg (0.25 mmol) of 1H-tetrazole dissolved in 0.5 ml of DMF were added, 7.8 µl (0.098 mmol) of 1-methylimidazole and 0.13 ml (0.40 mmol) of CEOP(N(i-Pr)$_2$)$_2$ were further added, and the mixture was stirred for two and a half hours at room temperature. The product was extracted with EtOAc and sat. NaHCO$_3$ aq., and the organic layer was washed with sat. NaCl aq. and dried with Na$_2$SO$_4$. The solvent was distilled off under reduced pressure, and the residue was purified by silica gel column chromatography (Hexane:EtOAc=1:1) to obtain a colorless foamy compound (20) (0.18 g, 0.20 mmol, 73%).

$^{31}$P NMR (162 MHz, CDCl$_3$) δ: 150.5, 148.7; HRMS (ESI) m/z Calcd for C$_{45}$H$_{55}$F$_3$KN$_5$NaO$_{10}$P (M+K)$^+$; 952.32757 found 952.32498.

(Method for Synthesizing CPG Resin)

The nucleoside derivative obtained above was converted to a CPG resin derivative as follows.

The compound 19 was dissolved in 1.5 ml of pyridine in an Ar atmosphere, 0.056 g of succinic anhydride and 0.034 g of DMAP were added, and the mixture was stirred for 20 hours at room temperature. The product was then extracted with EtOAc and distilled water, and the organic layer was washed with sat. NaHCO$_3$ aq. and sat. NaCl aq., and dried with Na$_2$SO$_4$. The solvent was distilled off under reduced pressure, the resulting residue was dissolved in 1.4 ml of DMF in an Ar atmosphere, 0.21 g of CPG resin (CPG-500 Å, NH$_2$ loading: 167 µmol/g) and 0.028 g of EDC.HCl were added, and the mixture was left standing for 5 days at room temperature. The reaction solution was filtered, and the residue was washed with pyridine. A mixture of 13.5 ml of pyridine, 0.183 g of DMAP and 1.5 ml of acetic anhydride was then added to the residue, which was then left standing for 1 day. The reaction solution was filtered, and the residue was washed with pyridine, EtOH and CH$_3$CN and dried under reduced pressure to obtain a 25.2 µmol/g CPG resin.

Second Embodiment (Oligonucleotide Synthesis)

Oligonucleotide synthesis was performed on a 0.2 µmol scale by the phosphoramidite method using an automatic nucleic acid synthesizer. A natural nucleoside amidite was diluted to 0.1 M with MeCN, CPG resin having the 3' terminal nucleoside bound thereto was packed in a column in an amount corresponding to 0.2 µmol based on the activity of each, and synthesis was initiated.

After completion of synthesis, the CPG resin was transferred to a sampling tube, 900 µl of CH$_3$CN and 100 µl of Et$_2$NH were added, and the resin was vortexed for five minutes. Following spin-down, the supernatant was discarded, and the resin was washed twice with 1 ml of CH$_3$CN. 500 µl of CH$_3$NH$_2$ and 500 µl of NH$_3$ aq. were added, and the mixture was incubated for 10 minutes at 65° C. The solution was returned to room temperature, the supernatant was transferred to an Eppendorf tube, the CPG resin was washed twice with 1 ml of 3:1 (v/v) H$_2$O/EtOH, and the solution was vacuum dried. This served to both excise the oligonucleotide from the CPG resin and deprotect the oligonucleotide.

The incubated sample was vacuum dried and then dissolved in DMSO (100 µl) to deprotect the TBDMS groups, and after addition of TEA.3HF (125 µl) the sample was stirred and then incubated for 90 minutes at 65° C. The incubated sample was increased to 10 ml with 0.1 M TEAA buffer, and the diluted solution was passed through an equilibrated Sep-Pac tC18 reverse-phase column and adsorbed on the column. The column was washed with sterile water to remove salts and eluted with 50% CH$_3$CN in H$_2$O (3 ml) to perform crude purification.

The crudely purified sample was vacuum dried, the residue was dissolved in loading solution (1×TBE in 90% formamide, 200 µl), and the target oligonucleotide was separated by 20% PAGE (500 V, 20 mA). The target oligonucleotide band was collected, 0.1 M TEAA buffer and 1 mM EDTA aqueous solution (20 ml) were added, and the mixture was shaken overnight. After shaking, the filtrate was passed through an equilibrated Sep-Pac tC18 reverse-phase column and adsorbed on the column. The column was washed with sterile water to remove salts, eluted with 50% MeCN in H$_2$O (3 ml), and vacuum dried.

The oligonucleotide was dissolved in H$_2$O (1 ml), and the yield was determined from the absorbance of the diluted solution at 260 nm. Oligonucleotide equivalent to 60 pmol was also vacuum dried, thoroughly mixed with 3 µl of sterile water and 3 µl of matrix solution and dried on a plate, and the mass was measured by MALDI-TOF/MS. The synthesized oligonucleotides are shown below.

TABLE 1

| Name | Sequence | SEQ ID |
| --- | --- | --- |
| ON 1 | 5'-GGC C<u>U</u>U <u>U</u>CA C<u>U</u>A C<u>U</u>C C<u>U</u>A C<u>U</u>U-3' | 1 |
| ON 2 | 5'-GGC C<u>U</u>U <u>U</u>CA C<u>U</u>A CUC C<u>U</u>A C<u>U</u>U-3' | 1 |
| ON 3 | 5'-GGC C<u>U</u>U <u>U</u>CA C<u>U</u>A C<u>U</u>C C<u>U</u>A C<u>U</u>U-3' | 1 |
| ON 4 | 5'-F U<u>U</u>C UUC <u>U</u>UC <u>U</u>U-3' | 2 |

In the table above, "U" represents the structure shown below, and F represents a fluorescent label.

[C9]

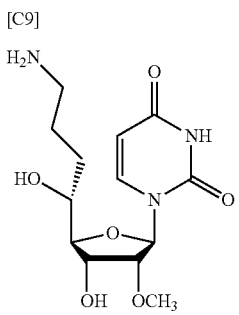

The reagents used are explained below.

(Teaa Buffer)

For the 0.1 M TEAA buffer, 2 N TEAA buffer (prepared by adding 277.6 ml of Et$_3$N to 114.38 ml of acetic acid, adding H$_2$O to a total of 1,000 ml and adjusting the pH to 7.0) was diluted 20 times and used.

(PAGE)

40% acrylamide (19:1) solution (40 ml), urea (33.6 g) and 10×TBE buffer (8 ml) were added and dissolved, and H$_2$O was added to a total of 80 ml. Finally APS (55 mg) was added and dissolved, TEMED (40 µl) was added and shaken, and the mixture was poured between two glass plates fixed with a 1.5 mm in between, and fixed by being left for at least one hour. 1×TBE buffer was also used as an electrophoresis buffer.

(1 mM EDTA Aqueous Solution)

0.1 M EDTA aqueous solution (1.80 g of EDTA.4Na prepared to 40 ml with H$_2$O) was diluted 100 times and used.

(Oligonucleotide Aqueous Solution)

An aqueous solution was obtained by diluting so that the absorbance at a wavelength of 260 nm (Abs260) was within the effective range of the absorbance meter. Abs260 was measured at room temperature using an absorbance measurement quartz cell with an optical path length (l) of 1 cm. The following formula was used for calculating OD$_{260}$. V here represents the total amount of the solution.

$$OD_{260}(M\varepsilon^{-1}\cdot ml^{-1}\cdot cm^{-1})=Abs_{260}(M\varepsilon^{-1})\cdot V^{-1}(ml^{-1})\cdot l^{-1} (cm^{-1})$$ [C10]

The molar extinction coefficient ($\varepsilon_{260}$) of the single-stranded oligonucleotide represented by $N_1pN_2pN_3p \ldots N_{n-1}N_n$ was calculated by the following formula.

$$\varepsilon=2\{\varepsilon(N_1pN_2)+\varepsilon(N_2pN_3)+ \ldots +\varepsilon(N_{n-1}pN_n)\}-\{\varepsilon(N_2)+\varepsilon(N_3)+ \ldots +\varepsilon(N_{n-1})\}$$ [C11]

$\varepsilon$ ($N_n$) here represents the $\varepsilon_{260}$ of the nucleic acid $N_n$, while c ($N_{n-1}pN_n$) represents the $\varepsilon_{260}$ of a nucleic acid dimer $N_{n-1}$ p$N_n$. The oligonucleotide was made into an aqueous solution and diluted so that the absorbance at a wavelength of 260 nm (Abs$_{260}$) was within the effective range of the absorption meter. Abs$_{260}$ was measured at room temperature using an absorbance measurement quartz cell with an optical path length (l) of 1 cm. The concentration C (mol/l) was calculated by the following formula.

$$C=Abs_{260}\cdot\varepsilon_{260}^{-1}\cdot l^{-1}$$ [C12]

(Matrix Solution)

The matrix solution was prepared by dissolving 3-hydroxypicolinic acid (3-HPA, 4.85 mg) and diammonium hydrogen citrate (0.8 mg) in 50 µl of 50% MeCN in H$_2$O. The diammonium hydrogen citrate was added to prevent attachment of Na$^+$ and K$^+$.

(40% Acrylamide (19:1) Solution)

This was prepared by dissolving acrylamide (190 g) and N,N'-bisacrylamide (10 g) in H$_2$O to a total of 500 ml.

(10×TBE Buffer)

This was prepared by dissolving Tris (109 g), boric acid (55 g) and EDTA.2Na (7.43 g) in H$_2$O to a total of 1,000 ml.

Third Embodiment (Measuring Nuclease Resistance)

300 pmol of the oligonucleotide ON4 synthesized in Second Embodiment were dissolved in 37.5 µl of OPTI-MEM, 1.1 µl was dispensed into an Eppendorf tube, and 5 µl of loading buffer was added to obtain a 0 min sample. 1.2 µl of bovine serum (BS) was added as a ribonuclease source to the remaining sample, and incubated at 37° C. After 15 minutes, 30 minutes, 1 hour, 3 hours, 6 hours, 12 hours and 24 hours, 2.4 µl were pipetted into an Eppendorf tube containing 10 µl of loading buffer on ice. These samples were electrophoresed and then analyzed with FUJIFILM LAS 4000. The results are shown in FIG. 1.

As shown in FIG. 1, while a naturally occurring oligonucleotide with a sequence identical to that of the oligonucleotide ON4 had been almost decomposed 6 to 12 hours after nuclease treatment, the oligonucleotide ON4 itself was preserved in a non-decomposed state even 12 hours and 24 hours after nuclease treatment.

Fourth Embodiment (Measuring Gene Expression Suppression Ability)

RNA interference was evaluated by a dual luciferase reporter assay.

HeLa cells were prepared to 8,000 cells/ml, added 100 µl per well to a 96-well plate, and cultured for 24 hours. The chains of the respective synthesized siRNAs were dissolved in TE buffer (100 mM NaCl), heated for three minutes at 100° C. and left for at least one hour, and returned to room temperature. 0.5 µl of siRNA solution, 48 µl of medium (OPTI-MEM) and 0.5 µl of RNAiMAX were mixed to a total volume of 50 µl, 40 µl of OPTI-MEM was added to each well of a 96-well plate from which the medium had been aspirated, and 10 µl of the prepared sample was then added to each well. This was then left for 1 hour at 37° C. in a CO$_2$ incubator, 100 µl of D-MEM was added to each well, and the cells were cultured for 24 hours at 37° C. in the CO$_2$ incubator. After 24 hours the medium was aspirated, and the plate was stored frozen for 24 hours. After thawing, luciferase luminescence was measured by adding 24 µl of dual glow substrate (firefly luciferase substrate), shaking for five minutes, transferring 23 µl of the sample to a 96-well plate for luminescence measurement, and measuring firefly luciferase. 23 µl of stop and glow substrate (Renilla luciferase substrate) was then added, the plate was shaken for 10 minutes, and Renilla luciferase was measured. The luminescence measurement for Renilla luciferase was divided by the value for firefly luciferase and compared using % of control. A naturally occurring oligonucleotide (Native) with an identical sequence was also used as a comparative example. Luminescenser JNRII was used for luciferase measurement. The results are shown in FIG. 2.

Figure 2:
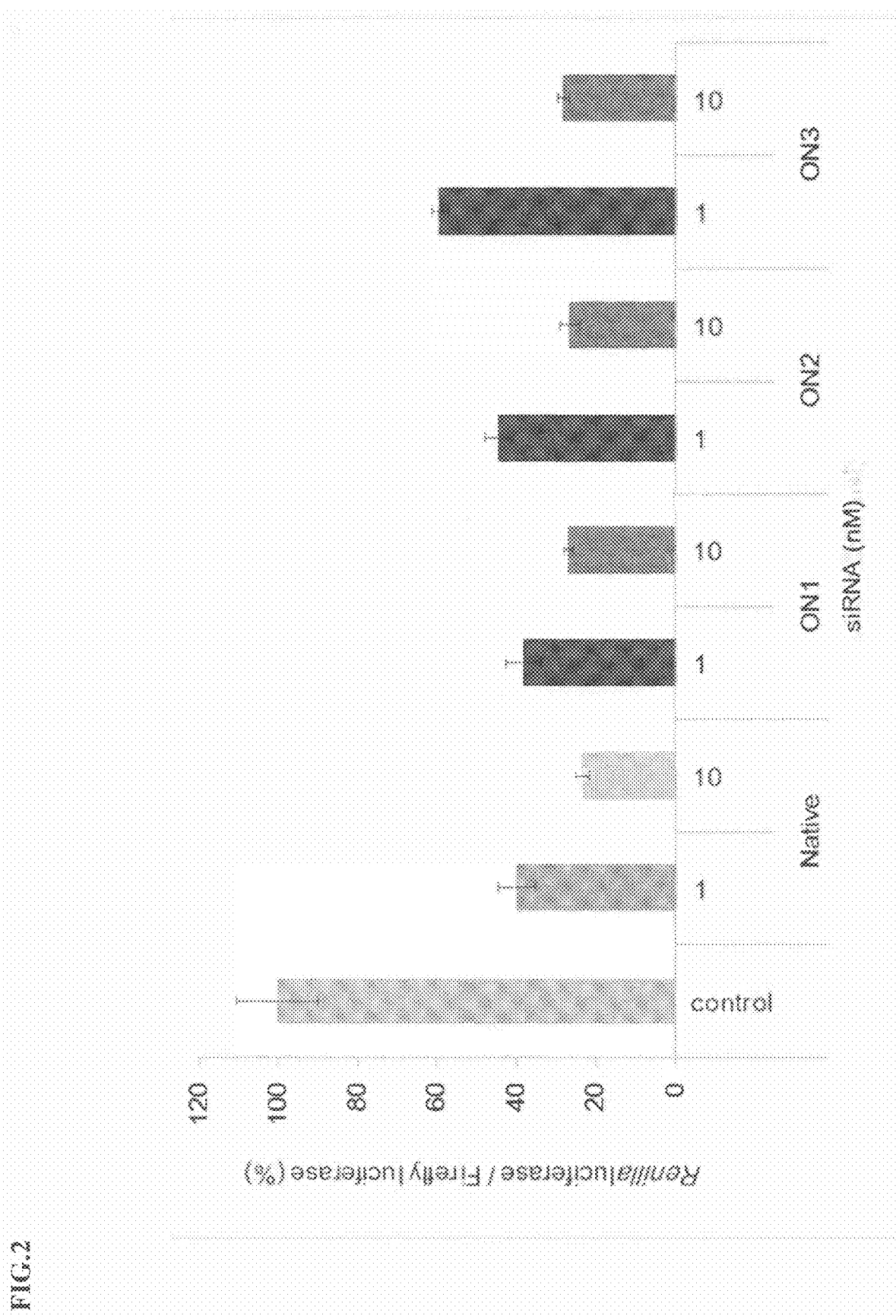
FIG. 2 shows the results of an evaluation of cell membrane permeability due to aminoalkyl group modification.

As shown in FIG. 2, the oligonucleotides ON1 to ON3 exhibited gene expression suppression ability equivalent to that of the naturally occurring oligonucleotide (Native).

Fifth Embodiment (Cell Membrane Permeability Test)

HeLa cells were prepared to 20,000 cells/ml, and 400 μl was added to each well of a 48-well plate and cultured for 24 hours. The oligonucleotide ON4 (40 pmol) dried on the Eppendorf tube was dissolved in OPTI-MEM (400 μl), and the entire amount was added to the wells after the medium had been aspirated from each well. After one hour of incubation, 200 μl/well of culture medium containing bovine serum (10% BS D-MEM (WAKO)) was added. After 24 hours, the medium was aspirated from each well, and the wells were washed twice with 1×PBS. The cells were then observed with an inverted fluorescence microscope (IX70, Olympus), with the results shown in FIG. 3. A naturally occurring oligonucleotide (Native) with an identical sequence was also used as a comparative example.

Figure 3:
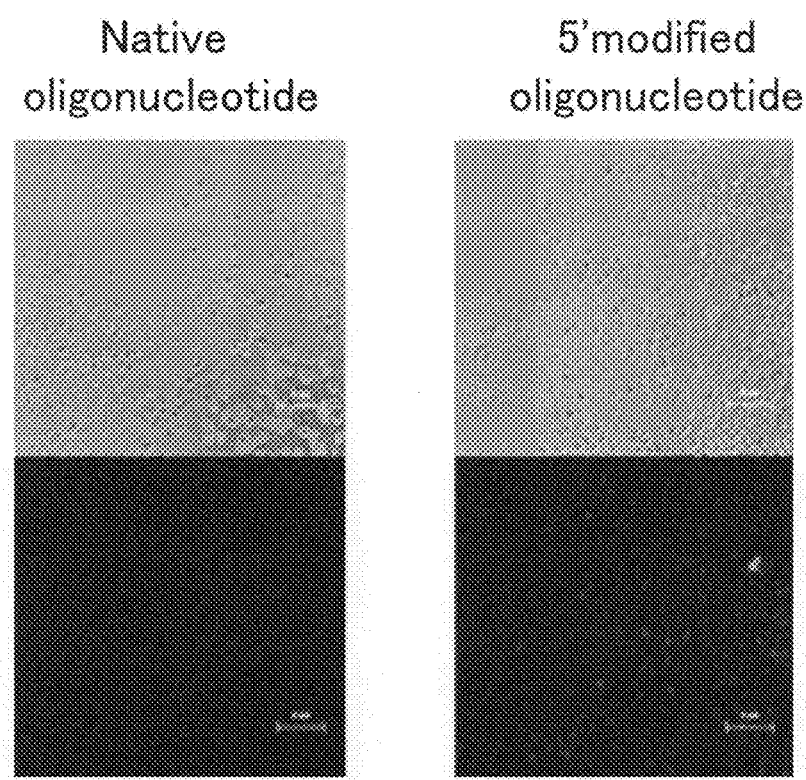
FIG. 3 shows the results of another evaluation of cell membrane permeability due to aminoalkyl group modification.

As shown in FIG. 3, while the naturally occurring oligonucleotide (Native) hardly penetrated the cell membrane, the oligonucleotide ON4 exhibited excellent cell membrane permeability.

Sixth Embodiment (2) Synthesis of 2'OCH$_3$-5' aminoethylamidite unit

A 2'OCH$_3$-5' aminoethylamidite unit and resin was synthesized according to the following scheme.

[C13]

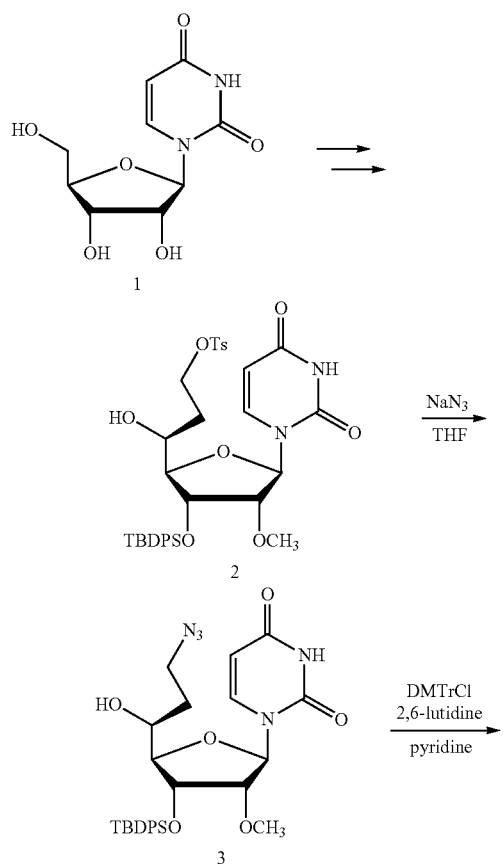

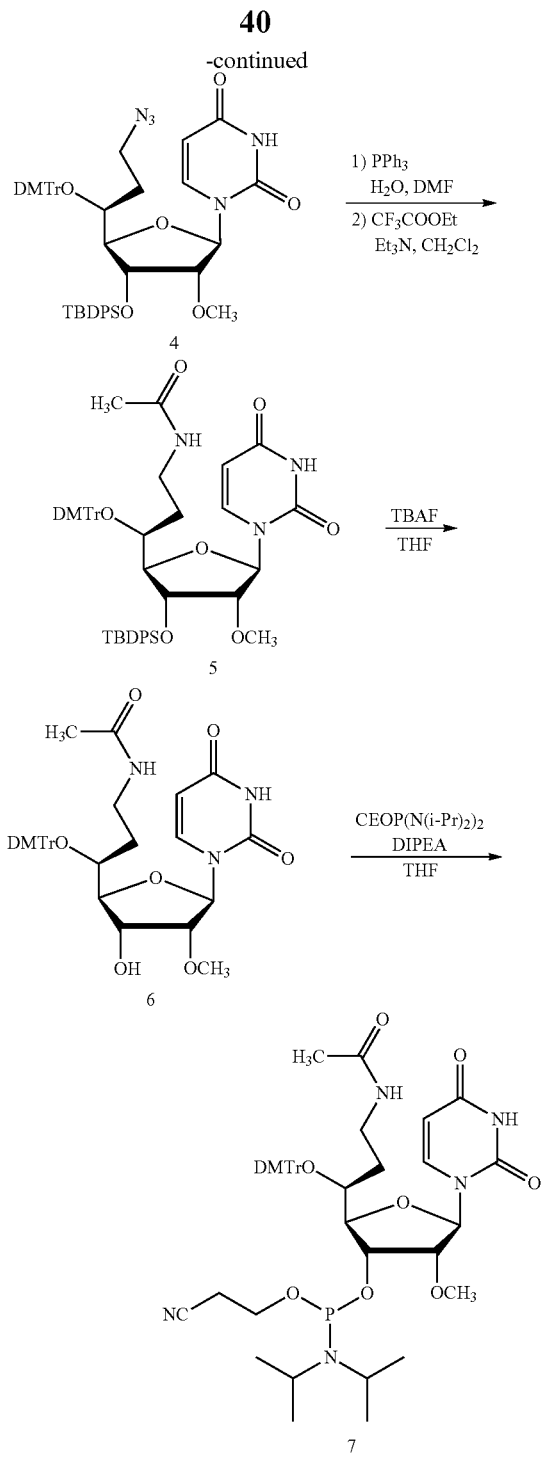

(S)-5'-C-Azidoethyl-3'-O-[(1, 1-dimethylethyl) diphenyl silyl]-2'-O-methyl-uridine (3)

Compound (2) (compound 15 in scheme 2 of Marie et al) was obtained according to the scheme 2 described by Marie Maturano et al., Eur. J. Org. Chem., 721-730 (2012) using uridine (compound (1)) as a starting material, 0.25 g (0.36 mmol) of the compound (2) were dissolved in 2.5 ml of DMF in an Ar atmosphere, 0.20 g (3.0 mmol) of NaN$_3$ were added, and the mixture was stirred for 18 hours at 60° C. The product was extracted from the reaction solution with EtOAc and sat. NaCl aq., and the organic layer was washed with sat. NaCl aq. and dried with $Na_2SO_4$. The solvent was distilled off under reduced pressure, and the residue was purified by silica gel column chromatography (Hexane:EtOAc=1:2) to obtain a white foamy compound (3) (0.19 g, 0.34 mmol, 95%).

$^1$H NMR (400 MHz, $CDCl_3$) δ: 8.01 (s, 1H), 7.71-7.57 (m, 4H), 7.58 (d, J=8.2 Hz, 1H), 7.51-7.39 (m, 6H), 5.67 (d, J=4.1 Hz, 1H), 5.63 (dd, J=8.2, 2.3 Hz, 1H), 4.19 (t, J=4.6 Hz, 1H), 3.91 (dd, J=5.0, 1.8 Hz, 1H), 3.78 (t, J=4.6 Hz, 1H), 3.41 (s, 3H), 3.34 (t, J=6.0 Hz, 1H), 2.21 (s, 1H), 1.77-1.71 (m, 1H), 1.52-1.51 (m, 1H), 1.11 (s, 9H).

(S)-5'-C-Azidoethyl-5'-O-(4, 4'-dimethoxytrityl)-3'-O-[(1, 1-dimethylethyl) diphenyl silyl]-2'-O-methyl-uridine (4)

0.19 g (0.34 mmol) of the compound (3) were dissolved in 2.0 ml of pyridine in an Ar atmosphere, 0.58 g (1.70 mmol) of DMTrCl and 0.23 ml (2.03 mmol) of 2,6-lutidine were added, and the mixture was stirred for 3 days at 40° C. The product was extracted from the reaction solution with EtOAc and distilled water, and the organic layer was washed with sat. NaCl aq. and dried with $Na_2SO_4$. The solvent was distilled off under reduced pressure, and the residue was purified by silica gel column chromatography (Hexane:EtOAc=1:1) to obtain a yellow foamy compound (4) (0.21 g, 0.24 mmol, 71%).

$^1$H NMR (600 MHz, $CDCl_3$) δ: 8.03 (d, J=8.2 Hz, 1H), 7.99 (d, J=2.0 Hz, 1H), 7.60-7.58 (m, 2H), 7.47 (d, J=6.9 Hz, 2H), 7.44-7.39 (m, 2H), 7.33 (t, J=7.6 Hz, 2H), 7.28-7.25 (m, 3H), 7.23 (s, 4H), 7.13-7.08 (m, 4H), 6.77-6.73 (m, 4H), 6.14 (d, J=5.5 Hz, 1H), 5.63 (dd, J=8.2, 2.7, 1H), 4.38 (dd, J=4.8, 3.4 Hz, 1H), 3.96 (t, J=2.7 Hz, 1H), 3.80 (s, 3), 3.79 (s, 3H), 3.68 (t, J=5.5 Hz, 1H), 3.28 (m, 1H), 3.13 (s, 3H), 2.57-2.52 (m, 1H), 2.74-2.70 (m, 1H), 1.80-1.74 (m, 1H), 1.36-1.30 (m, 1H), 0.99 (s, 9H).

(S)-5'4)-(4, 4'-dimethoxytrityl)-3'-O-[(1, 1-dimethylethyl) diphenyl silyl]-2'-O-methyl-5'-C-trifluoro-acetylaminopropyl-uridine (5)

0.21 g (0.24 mmol) of the compound (4) were dissolved in 4.0 ml of THF in an Ar atmosphere, 0.15 g (0.60 mmol) of $Ph_3P$ and 0.17 ml (9.68 mmol) of distilled water were added, and the mixture was stirred for 14 hours at 40° C. The solvent was distilled off under reduced pressure, the residue was dissolved in 2.5 ml of $CH_2Cl_2$, 50 μl (0.36 mmol) of $Et_3N$ and 87 μl (0.73 mmol) of $CF_3COOEt$ were added, and the mixture was stirred for 11 hours. The reaction solution was distilled under reduced pressure, the product was extracted with EtOAc and distilled water, and the organic layer was washed with sat. NaCl aq. and dried with $Na_2SO_4$. The solvent was distilled off under reduced pressure, and the residue was purified by silica gel column chromatography (Hexane:EtOAc=1:1) to obtain a yellow foamy compound (5) (0.19 g, 0.20 mmol, 83%).

$^1$H NMR (600 MHz, $CDCl_3$) δ: 8.11 (s, 1H), 7.96 (d, J=8.3 Hz, 1H), 7.60-7.59 (m, 2H), 7.48 (d, J=6.2 Hz, 2H), 7.45-7.38 (m, 2H), 7.34 (t, J=7.6 Hz, 2H), 7.28-7.22 (m, 6H), 7.15-7.11 (m, 4H), 6.77-6.74 (m, 4H), 6.08 (s, J=5.5 Hz, 1H), 5.84 (s, 1H), 5.66 (dd, J=8.2, 2.7 Hz, 1H), 4.41 (t, J=4.8 Hz, 1H), 3.92 (dd, J=3.4, 2.0 Hz, 1H), 3.79 (s, 3H), 3.79 (s, 3H), 3.64 (t, J=5.5 Hz, 1H), 3.24-3.21 (m, 1H), 3.13 (s, 3H), 2.80-2.69 (m, 2H), 1.72-1.66 (m, 1H), 1.32-1.28 (m, 1H), 0.98 (s, 9H).

(S)-5'4)-(4, 4'-dimethoxytrityl)-2'-O-methyl-5'-C-trifluoroacetylaminopropyl-uridine (6)

0.19 g (0.20 mmol) of the compound (5) were dissolved in 2.0 ml of THF in an Ar atmosphere, and 0.30 ml (0.30 mmol) of 1 M TBAF were added and stirred for 10 hours at room temperature. The solvent was distilled off under reduced pressure, and the residue was purified by silica gel column chromatography (Hexane:EtOAc=1:1) to obtain a white foamy compound (6) (0.12 g, 0.17 mmol, 85%).

$^1$H NMR (400 MHz, $CDCl_3$) δ: 8.56 (s, 1H), 7.82 (d, J=8.2 Hz, 1H), 7.43-7.41 (m, 2H), 7.35-7.23 (m, 6H), 6.85-6.81 (m, 4H), 6.23 (s, 1H), 5.84 (d, J=2.3 Hz, 1H), 5.65 (dd, J=8.3, 2.3 Hz, 1H), 4.16-4.11 (m, 1H), 3.94 (dd, J=7.4, 3.4 Hz, 1H), 3.83-3.81 (m, 1H), 3.80 (s, 3H), 3.79 (s, 3H), 3.70-3.68 (m, 1H), 3.59 (s, 3H), 3.28-3.12 (m, 2H), 2.53 (d, J=8.3 Hz, 1H), 1.80-1.71 (m, 1H), 1.65-1.61 (m, 1H).

3'-O-[2-Cyanoethoxy(diisopropylamino)phosphino]-(S)-5'-O-(4, 4'-dimethoxytrityl)-2'-O-methyl-5'-C-trifluoroacetylaminopropyl-uridine (7)

0.14 g (0.20 mmol) of the compound (6) were dissolved in 1.5 ml of THF in an Ar atmosphere, 0.17 ml (0.96 mmol) of DIPEA and 0.088 ml (0.39 mmol) of CEP-Cl were added, and the mixture was stirred for 30 minutes at room temperature. The product was extracted with $CHCl_3$ and sat. $NaHCO_3$ aq., and the organic layer was washed with sat. NaCl aq. and dried with $NaSO_4$. The solvent was distilled off under reduced pressure, and the residue was purified by silica gel column chromatography (Hexane:EtOAc=1:2) to obtain a white foamy compound (7) (0.14 g, 0.15 mmol, 77%).

$^{31}$P NMR (162 MHz, $CDCl_3$) δ: 150.8, 150.6.

Using the above scheme, a 5'-tosyloxyethyl compound such as the compound 2 can be obtained by a short process through a stereoselective aldol reaction using uridine or a nucleoside derivative such as 2'-O-alkyluridine as a starting material, and the desired amidite agent can be efficiently obtained as a result.

All documents referred to in the specification of the present application are hereby incorporated by reference in their entirety.

SEQUENCE LISTING FREE TEXT

SEQ ID NOs.1-2: Artificial siRNA

The invention claimed is:

1. An oligonucleotide comprising a nucleoside derivative represented by formula (1) or (2) below, or a salt thereof:

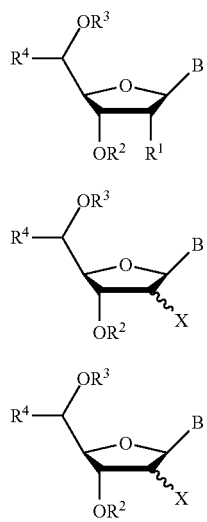

wherein:
R$^1$ represents
a hydroxyl group,
a hydroxyl group in which a hydrogen atom is substituted by an alkyl group or
alkenyl group, or
a protected group,
X represents a halogen atom;
R$^2$ and R$^3$ may be the same or different, and each represents
a hydrogen atom,
a hydroxyl protecting group,
a phosphate group,
a protected phosphate group, or
—P(=O)$_n$R$^5$R$^6$ (in which n is 0 or 1, and R$^5$ and R$^6$ may be the same or different, with each representing a hydrogen atom, hydroxyl group, protected hydroxyl group, mercapto group, protected mercapto group, lower alkoxy group, cyano lower alkoxy group, amino group or substituted amino group, but when n is 1, R$^5$ and R$^6$ are not both hydrogen atoms), R$^4$ represents NHR$^7$ (in which R$^7$ represents a hydrogen atom, an alkyl group, an alkenyl group or a protecting group for an amino group), an azide group, an amidino group or a guanidino group, each having a linking group that is an alkylene group having two to eight carbon atoms, and B represents a nucleobase.

2. The oligonucleotide according to claim 1, wherein either R$^7$ represents a hydrogen atom or R$^4$ represents the guanidino group having a linking group.

3. The oligonucleotide according to claim 1, wherein the linking group of R$^4$ in formulae (1) and (2) above is an alkylene group having two or three carbon atoms.

4. The oligonucleotide according to claim 1, wherein said oligonucleotide comprises cell membrane permeability properties.

5. A ribonuclease resistance imparting agent comprising the oligonucleotide according to claim 1.

6. The oligonucleotide according to claim 1, wherein said oligonucleotide comprises at least two of said nucleoside derivative.

7. The oligonucleotide according to claim 1, wherein said oligonucleotide comprises a least three of said nucleoside derivative.

8. The oligonucleotide according to claim 1, wherein said oligonucleotide comprises 3 to 8 of said nucleoside derivative.

9. The oligonucleotide according to claim 1, comprising at least 3 of said nucleoside derivative positioned roughly equally at the 5' end, the center and the 3' end of the oligonucleotide.

10. The oligonucleotide according to claim 1, wherein said oligonucleotide consists of a siRNA.

11. The oligonucleotide according to claim 1, wherein said oligonucleotide is selected from the group consisting of a DNA molecule, a RNA molecule, and a duplex comprising a DNA and/or a RNA molecule.

12. The oligonucleotide according to claim 1, wherein said oligonucleotide consists of a RNA molecule.

13. The oligonucleotide according to claim 1, wherein said nucleoside derivative consists of one of the following structures:

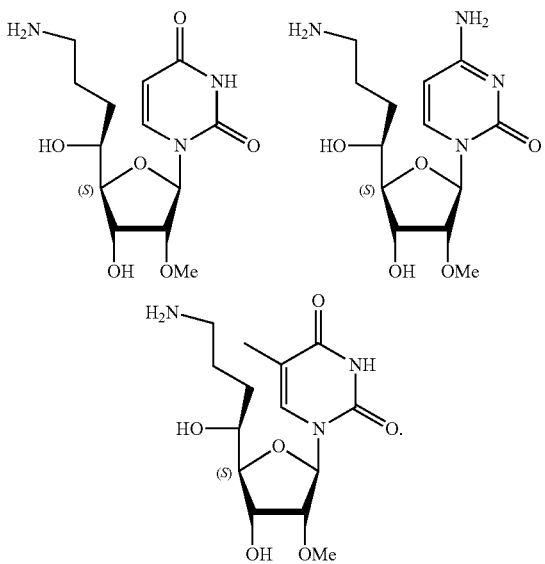

14. A RNA molecule comprising an oligoribonucleotide derivative represented by represented by formula (1) or (2) below, or a salt thereof:

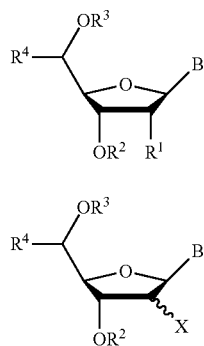

wherein:
$R^1$ represents
a hydroxyl group,
a hydroxyl group in which a hydrogen atom is substituted by an alkyl group or alkenyl group, or
a protected group,
X represents a halogen atom,
$R^2$ and $R^3$ may be the same or different, and each represents
a hydrogen atom,
a hydroxyl protecting group,
a phosphate group,
a protected phosphate group, or
$-P(=O)_n R^5 R^6$ (in which n is 0 or 1, and $R^5$ and $R^6$ may be the same or different,
with each representing a hydrogen atom, hydroxyl group, protected hydroxyl
group, mercapto group, protected mercapto group, lower alkoxy group, cyano lower alkoxy group, amino group or substituted amino group, but when n is 1, $R^5$ and $R^6$ are not both hydrogen atoms),
$R^4$ represents $NHR^7$ (in which $R^7$ represents a hydrogen atom, an alkyl group, an alkenyl group or a protecting group for an amino group), an azide group, an amidino group or a guanidino group, each having a linking group that is an alkylene group having two to eight carbon atoms, and
B represents a purine-9-yl group, 2-oxo-pyrimidin-l-yl group, substituted purine-9-yl group or substituted 2-oxo-pyrimidin-l-yl group.

15. The RNA molecule according to claim 14, wherein $R^2$ and $R^3$ each represents a hydrogen atom.

16. The RNA molecule according to claim 14, wherein $R^7$ represents a hydrogen atom.

17. The RNA molecule according to claim 14, wherein said RNA molecule comprises a least three of said nucleoside derivative.

18. The RNA molecule according to claim 14, wherein said RNA molecule comprises 3 to 8 of said nucleoside derivative.

19. The RNA molecule according to claim 14, comprising at least 3 of said nucleoside derivative positioned roughly equally at the 5' end, the center and the 3' end of the RNA molecule.

20. The RNA molecule according to claim 14, wherein said RNA molecule consists of a siRNA.

* * * * *

SEQUENCE LISTING

<160> NUMBER OF SEQ ID NOS: 2

<210> SEQ ID NO 1
<211> LENGTH: 21
<212> TYPE: RNA
<213> ORGANISM: Artificial Sequence

```
<220> FEATURE:
<223> OTHER INFORMATION: Synthetic siRNA

<400> SEQUENCE: 1
ggccuuucac uacuccuacu u                                    21

<210> SEQ ID NO 2
<211> LENGTH: 11
<212> TYPE: RNA
<213> ORGANISM: Artificial Sequence
<220> FEATURE:
<223> OTHER INFORMATION: Synthetic siRNA

<400> SEQUENCE: 2
uucuucuucu u                                               11
```